(12) United States Patent
Fujiwara et al.

(10) Patent No.: US 10,344,312 B2
(45) Date of Patent: *Jul. 9, 2019

(54) BLOOD COMPONENT MEASUREMENT DEVICE AND BLOOD COMPONENT MEASUREMENT METHOD

(71) Applicant: PHC HOLDINGS CORPORATION, Tokyo (JP)

(72) Inventors: Masaki Fujiwara, Ehime (JP); Tomohiro Yamamoto, Osaka (JP)

(73) Assignee: PHC Holdings Corporation, Tokyo (JP)

( * ) Notice: Subject to any disclaimer, the term of this patent is extended or adjusted under 35 U.S.C. 154(b) by 38 days.

This patent is subject to a terminal disclaimer.

(21) Appl. No.: 15/651,640

(22) Filed: Jul. 17, 2017

(65) Prior Publication Data
US 2018/0127795 A1 May 10, 2018

Related U.S. Application Data

(62) Division of application No. 14/895,785, filed as application No. PCT/JP2014/003599 on Jul. 7, 2014, now Pat. No. 9,738,916.

(30) Foreign Application Priority Data

Jul. 8, 2013 (JP) .................. 2013-142728
Jul. 8, 2013 (JP) .................. 2013-142737

(51) Int. Cl.
*C12Q 1/26* (2006.01)
*C12Q 1/00* (2006.01)
*G01N 27/327* (2006.01)

(52) U.S. Cl.
CPC .............. *C12Q 1/006* (2013.01); *C12Q 1/26* (2013.01); *G01N 27/3274* (2013.01)

(58) Field of Classification Search
CPC ....................................................... C12Q 1/26
See application file for complete search history.

(56) References Cited

U.S. PATENT DOCUMENTS 4,731,726 A 3/1988 Allen, III
5,366,609 A 11/1994 White et al.
(Continued)

FOREIGN PATENT DOCUMENTS

EP 2 577 303 4/2013
JP 2009-258129 11/2009
(Continued)

OTHER PUBLICATIONS

International Search Report issued in International Application No. PCT/JP2014/003599, 4 pages, dated Oct. 7, 2014.
(Continued)

*Primary Examiner* — Rosanne Kosson
(74) *Attorney, Agent, or Firm* — Hamre, Schumann, Mueller & Larson, P.C.

(57) ABSTRACT

Provided are a blood component measurement device and the like capable of further suppressing the errors in measuring blood components. A first current value that is generated by oxidation-reduction when a first voltage is applied to a first electrode pair 21, 22 composing a biosensor 1 is measured, a second current value that is generated when a second voltage is applied to a second electrode pair 23, 24 composing the biosensor 1 is measured, and then the first current and the second current are converted to give a blood component amount. Within a predetermined period after the introduction of blood into the biosensor 1, the first current is measured multiple times and the second current is measured once. A CPU 72 converts a plurality of first current values and the second current value to obtain a plurality of blood component amounts and calculates the blood component
(Continued)

amount for the blood introduced into the biosensor 1 from said plurality of blood component amounts.

4 Claims, 12 Drawing Sheets

(56) References Cited

U.S. PATENT DOCUMENTS

| | | | |
|---|---|---|---|
| 9,816,957 B2* | 11/2017 | Fujiwara | G01N 27/3274 |
| 2007/0087397 A1 | 4/2007 | Kraft et al. | |
| 2007/0131565 A1 | 6/2007 | Fujiwara et al. | |
| 2007/0138026 A1 | 6/2007 | Fujiwara et al. | |
| 2009/0242425 A1 | 10/2009 | Kamath et al. | |
| 2011/0203942 A1 | 8/2011 | Uchiyama | |
| 2012/0111739 A1* | 5/2012 | Pasqua | G01N 27/3271 205/777.5 |

FOREIGN PATENT DOCUMENTS

| | | |
|---|---|---|
| JP | 2011-506964 | 3/2011 |
| JP | 2011-232360 | 11/2011 |
| WO | 2005/103669 | 11/2005 |
| WO | 2009/075951 | 6/2009 |
| WO | 2010/061629 | 6/2010 |
| WO | 2011/156325 | 12/2011 |

OTHER PUBLICATIONS

Nguyen, et al., "Trade-Off Between Sample Size and Accuracy: Case of Dynamic Measurements under Interval Uncertainty", University of Texas at El Paso, Departmental Technical Reports (CS), Department of Computer Science, DigitalCommons@UTEP, Oct. 1, 2007, paper 196, http://digitalcommons.utep.edu/cgi/viewcontent.cgi?article=1195&context=cs_techrep.

Nguyen, et al., "Trade-off between sample size and accuracy: Case of Measurements under interval uncertainty", International Journal of Approximate Reasoning 50 (2009) 1164-1176.

Office Action issued in corresponding Chinese patent application No. 201480039211.4, dated Mar. 1, 2017, 17 pages with an English translation.

Office Action issued in corresponding Chinese Patent Application No. 201480039211.4, dated Nov. 1, 2017, 7 pages with an English translation.

Office Action issued in corresponding European Patent Application No. 14822488.4, dated Aug. 30, 2018, 4 pages.

* cited by examiner

ID COMPONENT MEASUREMENT DEVICE AND BLOOD COMPONENT MEASUREMENT METHOD

BLOOD COMPONENT MEASUREMENT DEVICE AND BLOOD COMPONENT MEASUREMENT METHOD

TECHNICAL FIELD

The present invention relates to a blood component measurement device and a blood component measurement method for measuring a component contained in blood.

BACKGROUND ART

Patent Document 1 mentioned below describes a sensor system, etc. for determining the concentration of an analyte in a sample. This sensor system inputs input signals including multiple duty cycles of sequential excitation pulses and relaxations into the sample. Thereby, one or more signals output from the sample within 300 ms after the input of an excitation pulse are correlated with the analyte concentration of the sample, which allows the accuracy and/or precision of the analysis to be improved.

PRIOR ART DOCUMENTS

Patent Documents

[Patent Document 1] JP 2011-506964 A

DISCLOSURE OF INVENTION

Problem to be Solved by the Invention

The above-described sensor system inputs pulses multiple times into the sample. However, since the analyte concentration of the sample is determined using the output signal itself, the measurement errors are not suppressed sufficiently.

Thus, with the above situation in mind, the present invention has been proposed and is intended to provide a blood component measurement device and a blood component measurement method that can further suppress the errors in measuring blood components.

Means for Solving Problem

A blood component measurement device according to a first aspect of the present invention (hereinafter may be referred to as a "first blood component measurement device") is a blood component measurement device that measures a blood component amount using a biosensor in which blood is introduced and then a blood component contained in said blood is subjected to oxidation-reduction using an oxidoreductase, wherein the blood component measurement device includes: a first current value measurement means that detects, as a first current value, an oxidation-reduction current that is generated by the oxidation-reduction when a first voltage is applied to a first electrode pair composing the biosensor; a second current value measurement means that detects, as a second current value, a current that is generated when a second voltage is applied to a second electrode pair composing the biosensor; a control means that exerts control so that, over a predetermined period after the introduction of the blood into the biosensor, the first current value measurement means measures the first current value multiple times, with the first voltage being continuously applied to the first electrode pair, and the second current value measurement means measures the second current value in a late stage of the predetermined period, with the second voltage being applied; a conversion means that converts, to blood component amounts, pairs of any one of a plurality of first current values measured by the first current value measurement means and the second current value measured by the second current value measurement means; and a calculation means that calculates the blood component amount for the blood introduced into the biosensor, using a plurality of the blood component amounts converted by the conversion means.

A blood component measurement device according to a second aspect of the present invention is the blood component measurement device of the above-mentioned first aspect, wherein the blood component measurement device includes a storage means that contains recorded data, stored per blood in which the blood component amount is known, including a plurality of blood component amounts converted from pairs of any one of a plurality of first current values and a second current value, and the calculation means compares the recorded data with measured data including a plurality of the blood component amounts converted by the conversion means and calculates the blood component amount of the blood from which recorded data most approximated to said measured data was obtained, as the blood component amount of the blood introduced into the biosensor.

A blood component measurement device according to a third aspect of the present invention is the blood component measurement device of the above-mentioned first aspect, wherein the blood component measurement device includes a storage means that contains recorded data, stored per blood in which the blood component amount is known and per ambient temperature, including a plurality of blood component amounts converted from pairs of any one of a plurality of first current values and a second current value, and a temperature detection means that detects the ambient temperature, and the calculation means extracts a plurality of recorded data obtained at a temperature near the ambient temperature detected by the temperature detection means, compares the plurality of recorded data thus extracted with measured data including the plurality of the blood component amounts converted by the conversion means, and calculates the blood component amount of the blood from which recorded data most approximated to said measured data was obtained, as the blood component amount of the blood introduced into the biosensor.

A blood component measurement device according to a fourth aspect of the present invention is the blood component measurement device of the above-mentioned second or third aspect, wherein the calculation means compares a plurality of blood component amounts converted from arbitrary combinations of a first current value and the second current value selected from the plurality of first current values and the second current value measured as a result of the control exerted by the control means, with recorded data of a plurality of blood component amounts converted from the same combinations as the arbitrary combinations of a first current value and the second current value stored in the storage means, and calculates the blood component amount of the blood from which recorded data most approximated was obtained, as the blood component amount of the blood introduced into the biosensor.

A blood component measurement device according to a fifth aspect of the present invention is the blood component measurement device of any one of the above-mentioned second to fourth aspects, wherein the control means allows the first current value measurement means to measure the first current values during a first period included in the first half of the predetermined period and a second period included in the second half of the predetermined period.

A blood component measurement device according to a sixth aspect of the present invention is the blood component measurement device of the above-mentioned fifth aspect, wherein the control means allows the first current value measurement means to measure the first current value at least during a first period in which the temperature of the blood introduced into the biosensor changes greatly and a second period in which the temperature of the blood introduced into the biosensor is stable, within the predetermined period.

A blood component measurement device according to a seventh aspect of the present invention is the blood component measurement device of the above-mentioned first aspect, wherein the calculation means calculates the blood component amount of the blood introduced into the biosensor by multivariate analysis that is carried out using the plurality of the blood component amounts converted by the conversion means.

A blood component measurement method according to an eighth aspect of the present invention (hereinafter may also be referred to as a "first blood component measurement method") is a blood component measurement method in which a blood component amount is measured using a biosensor in which blood is introduced and then a blood component contained in said blood is subjected to oxidation-reduction using an oxidoreductase, wherein the blood component measurement method includes: a first current value measurement step for detecting, as a first current value, an oxidation-reduction current that is generated by the oxidation-reduction when a first voltage is applied to a first electrode pair composing the biosensor; a second current value measurement step for detecting, as a second current value, a current that is generated when a second voltage is applied to a second electrode pair composing the biosensor; a conversion step for converting, to blood component amounts, pairs of any one of a plurality of first current values measured in the first current value measurement step and the second current value measured in the second current value measurement step; and a calculation step for calculating the blood component amount contained in the blood using a plurality of the blood component amounts converted in the conversion step, wherein in the first current value measurement step, the first current value is measured multiple times over a predetermined period after the introduction of the blood into the biosensor, with the first voltage being continuously applied to the first electrode pair, and in the second current value measurement step, the second current value is measured in a late stage of the predetermined period, with the second voltage being applied, and in the conversion step, a plurality of blood component amounts are obtained from a plurality of first current values measured in the first current value measurement step and the second current value measured in the second current value measurement step.

A blood component measurement method according to a ninth aspect of the present invention is the blood component measurement method of the above-mentioned eighth aspect, wherein the calculation step includes: referring to recorded data, stored in a storage means per blood in which the blood component amount is known, including a plurality of the blood component amounts converted from pairs of any one of a plurality of first current values and a second current value; comparing the recorded data with measured data including the plurality of the blood component amounts converted in the conversion step; and calculating the blood component amount of the blood from which recorded data most approximated to said measured data was obtained, as the blood component amount of the blood introduced into the biosensor.

A blood component measurement method according to a tenth aspect of the present invention is the blood component measurement method of the above-mentioned eighth aspect, wherein the blood component measurement method includes a temperature detection step for detecting ambient temperature, and the calculation step includes: referring to recorded data, stored in a storage means per blood in which the blood component amount is known and per ambient temperature, including a plurality of blood component amounts converted from pairs of any one of a plurality of first current values and a second current value; extracting a plurality of recorded data obtained at a temperature near the ambient temperature detected in the temperature detection step; comparing said plurality of recorded data thus extracted with measured data including a plurality of the blood component amounts converted in the conversion step; and calculating the blood component amount of the blood from which recorded data most approximated to said measured data was obtained, as the blood component amount of the blood introduced into the biosensor.

A blood component measurement method according to an eleventh aspect of the present invention is the blood component measurement method of the above-mentioned ninth or tenth aspect, wherein in the calculation step, a plurality of blood component amounts converted from arbitrary combinations of a first current value and the second current value selected from the plurality of first current values measured in the first current value measurement step and the second current value measured in the second current value measurement step are compared with recorded data of a plurality of blood component amounts converted from the same combinations as the arbitrary combinations of a first current value and the second current value stored in the storage means, and the blood component amount of the blood from which recorded data most approximated was obtained is calculated as the blood component amount of the blood introduced into the biosensor.

A blood component measurement method according to a twelfth aspect of the present invention is the blood component measurement method of any one of the above-mentioned ninth to eleventh aspects, wherein in the first current value measurement step, the first current values are measured during a first period included in the first half of the predetermined period and a second period included in the second half of the predetermined period.

A blood component measurement method according to a thirteenth aspect of the present invention is the blood component measurement method of the above-mentioned twelfth aspect, wherein in the first current value measurement step, the first current value is measured at least during a first period in which the temperature of the blood introduced into the biosensor changes greatly and a second period in which the temperature of the blood introduced into the biosensor is stable, within the predetermined period.

A blood component measurement method according to a fourteenth aspect of the present invention is the blood component measurement method of the above-mentioned eighth aspect, wherein in the calculation step, the blood component amount of the blood introduced into the biosensor is calculated by multivariate analysis that is carried out using at least part of the plurality of first current values measured in the first current value measurement step and the second current value measured in the second current value measurement step.

A blood component measurement device according to a fifteenth aspect of the present invention (hereinafter may also be referred to as a "second blood component measurement device") is a blood component measurement device that measures a blood component amount using a biosensor in which blood is introduced and then a blood component contained in said blood is subjected to oxidation-reduction using an oxidoreductase, wherein the blood component measurement device includes: a first current value measurement means that detects, as a first current value, an oxidation-reduction current that is generated by the oxidation-reduction when a first voltage is applied to a first electrode pair composing the biosensor; a second current value measurement means that detects, as a second current value, a current that is generated when a second voltage is applied to a second electrode pair composing the biosensor; a control means that exerts control so that within a predetermined period after the introduction of the blood into the biosensor, the second current value measurement means applies the second voltage to the second electrode pair in the form of pulses to measure the second current value multiple times and the first current value measurement means measures the first current value at an arbitrary timing within the predetermined period; a conversion means that converts, to blood component amounts, pairs of the first current value measured by the first current value measurement means and any one of a plurality of second current values measured by the second current value measurement means; and a calculation means that calculates the blood component amount for the blood introduced into the biosensor, using a plurality of the blood component amounts converted by the conversion means.

A blood component measurement device according to a sixteenth aspect of the present invention is the blood component measurement device of the above-mentioned fifteenth aspect, wherein the blood component measurement device includes a storage means that contains recorded data, stored per blood in which the blood component amount is known, including a plurality of blood component amounts converted from pairs of a first current value and any one of a plurality of second current values, and the calculation means compares the recorded data with measured data including a plurality of the blood component amounts converted by the conversion means and calculates the blood component amount of the blood from which recorded data most approximated to said measured data was obtained, as the blood component amount of the blood introduced into the biosensor.

A blood component measurement device according to a seventeenth aspect of the present invention is the blood component measurement device of the above-mentioned fifteenth aspect, wherein the blood component measurement device includes a storage means that contains recorded data, stored per blood in which the blood component amount is known and per ambient temperature, including a plurality of blood component amounts converted from pairs of a first current value and any one of a plurality of second current values, and a temperature detection means that detects the ambient temperature, and the calculation means extracts a plurality of recorded data obtained at a temperature near the ambient temperature detected by the temperature detection means, compares said plurality of recorded data thus extracted with measured data including the plurality of the blood component amounts converted by the conversion means, and calculates the blood component amount of the blood from which recorded data most approximated to said measured data was obtained, as the blood component amount of the blood introduced into the biosensor.

A blood component measurement device according to an eighteenth aspect of the present invention is the blood component measurement device of the above-mentioned sixteenth or seventeenth aspect, wherein the calculation means compares a plurality of blood component amounts converted from arbitrary combinations of the first current value and the second current value selected from the first current value and the plurality of second current values measured as a result of the control exerted by the control means, with recorded data of a plurality of blood component amounts converted from the same combinations as the arbitrary combinations of the first current value and the second current value stored in the storage means, and calculates the blood component amount of the blood from which recorded data most approximated was obtained, as the blood component amount of the blood introduced into the biosensor.

A blood component measurement device according to a nineteenth aspect of the present invention is the blood component measurement device of any one of the sixteenth to eighteenth aspects, wherein the control means allows the second current value to be measured at least during a first period in which the temperature of the blood introduced into the biosensor changes greatly and a second period in which the temperature of the blood introduced into the biosensor is stable, within the predetermined period.

A blood component measurement device according to a twentieth aspect of the present invention is the blood component measurement device according to any one of the above-mentioned sixteenth to nineteenth aspects, wherein the control means controls the second current value measurement means so that the second voltage is applied to the second electrode pair continuously within the predetermined period and the plurality of second current values are measured at arbitrary timings.

A blood component measurement device according to a twenty-first aspect of the present invention is the blood component measurement device of any one of the above-mentioned sixteenth to twentieth aspects, wherein the control means controls the second current value measurement means so that the second voltage is applied to the second electrode pair multiple times in the form of pulses within the predetermined period and the second current value is measured at each timing at which the second voltage is applied.

A blood component measurement device according to a twenty-second aspect of the present invention is the blood component measurement device of the above-mentioned sixteenth aspect, wherein the calculation means calculates the blood component amount of the blood introduced into the biosensor by multivariate analysis that is carried out using the plurality of the blood component amounts converted by the conversion means.

A blood component measurement method according to a twenty-third aspect of the present invention (hereinafter may also be referred to as a "second blood component measurement method") is a blood component measurement method in which a blood component amount is measured using a biosensor in which blood is introduced and then a blood component contained in said blood is subjected to oxidation-reduction using an oxidoreductase, wherein the blood component measurement method includes: a first current value measurement step for detecting, as a first current value, an oxidation-reduction current that is generated by the oxidation-reduction when a first voltage is applied to a first electrode pair composing the biosensor; a second current value measurement step for detecting, as a second current value, a current that is generated when a second voltage is applied to a second electrode pair composing the biosensor; a conversion step for converting, to blood component amounts, pairs of the first current value measured in the first current value measurement step and any one of a plurality of second current values measured in the second current value measurement step; and a calculation step for calculating the blood component## amount introduced into the biosensor using a plurality of the blood component amounts converted in the conversion step, wherein in the first current value measurement step, the first current value is measured at an arbitrary timing within a predetermined period after the introduction of the blood into the biosensor, and in the second current value measurement step, the second voltage is applied to the second electrode pair in the form of pulses within the predetermined period and thereby the second current value is measured multiple times.

A blood component measurement method according to a twenty-fourth aspect of the present invention is the blood component measurement method of the above-mentioned twenty-third aspect, wherein the calculation step includes: referring to recorded data, stored in a storage means per blood in which the blood component amount is known, including a plurality of the blood component amounts converted from pairs of a first current value and any one of a plurality of second current values; comparing the recorded data with measured data including the plurality of the blood component amounts converted in the conversion step; and calculating the blood component amount of the blood from which recorded data most approximated to said measured data was obtained, as the blood component amount of the blood introduced into the biosensor.

A blood component measurement method according to a twenty-fifth aspect of the present invention is the blood component measurement method of the above-mentioned twenty-third aspect, wherein the blood component measurement method includes a temperature detection step for detecting ambient temperature, and the calculation step includes: referring to recorded data, stored in a storage means per blood in which the blood component amount is known and per ambient temperature, including a plurality of blood component amounts converted from pairs of a second current value and any one of a plurality of first current values; extracting a plurality of recorded data obtained at a temperature near the ambient temperature detected in the temperature detection step; comparing said plurality of recorded data thus extracted with measured data including a plurality of the blood component amounts converted in the conversion step; and calculating the blood component amount of the blood from which recorded data most approximated to said measured data was obtained, as the blood component amount of the blood introduced into the biosensor.

A blood component measurement method according to a twenty-sixth aspect of the present invention is the blood component measurement method of the above-mentioned twenty-fourth or twenty-fifth aspect, wherein in the calculation step, a plurality of blood component amounts converted from arbitrary combinations of the first current value and the second current value selected from the first current values and the plurality of second current values that were measured are compared with recorded data of a plurality of blood component amounts converted from the same combinations as the arbitrary combinations of the first current value and the second current value stored in the storage means, and the blood component amount of the blood from which recorded data most approximated was obtained is calculated as the blood component amount of the blood introduced into the biosensor.

A blood component measurement method according to a twenty-seventh aspect of the present invention is the blood component measurement method of any one of the above-mentioned twenty-third to twenty-sixth aspects, wherein in the second current value measurement step, the second current value is measured at least during a first period in which the temperature of the blood introduced into the biosensor changes greatly and a second period in which the temperature of the blood introduced into the biosensor is stable, within the predetermined period.

A blood component measurement method according to a twenty-eighth aspect of the present invention is the blood component measurement method of any one of the above-mentioned twenty-third to twenty-seventh aspects, wherein in the second current value measurement step, the second voltage is applied to the second electrode pair continuously within the predetermined period and the plurality of second current values are measured at arbitrary timings.

A blood component measurement method according to a twenty-ninth aspect of the present invention is the blood component measurement method of any one of the above-mentioned twenty-third to twenty-seventh aspects, wherein in the second current value measurement step, the second voltage is applied to the second electrode pair multiple times in the form of pulses within the predetermined period and the second current value is measured at each timing at which the second voltage is applied.

A blood component measurement method according to a thirtieth aspect of the present invention is the blood component measurement method of the above-mentioned twenty-third aspect, wherein in the calculation step, the blood component amount of the blood introduced into the biosensor is calculated by multivariate analysis that is carried out using the plurality of the blood component amounts converted in the conversion step.

A biosensor according to a thirty-first aspect of the present invention is a biosensor in which blood is introduced and then a blood component contained in said blood is subjected to oxidation-reduction using an oxidoreductase, wherein the biosensor includes: a first electrode pair in which a working electrode and a counter electrode contact with the oxidoreductase and a mediator; a second electrode pair including a working electrode that does not contact with the oxidoreductase and a mediator and a counter electrode that contacts with the oxidoreductase and the mediator but does not contact with the working electrode of the first electrode pair; and a non-interference portion that separates the working electrode of the first electrode pair from the counter electrode of the second electrode pair, and a first voltage is applied to the first electrode pair at an arbitrary timing within a predetermined period after the introduction of the blood into the biosensor, and a second voltage is applied to the second electrode pair multiple times in the form of pulses within the predetermined period.

A blood component measurement device according to a thirty-second aspect of the present invention (hereinafter may also be referred to as a "third blood component measurement device") is a blood component measurement device that measures a blood component amount using a biosensor in which blood is introduced and then a blood component contained in said blood is subjected to oxidation-reduction using an oxidoreductase, wherein the blood component measurement device includes:

a first current value measurement means that detects, as a first current value, an oxidation-reduction current that is generated by the oxidation-reduction when a first voltage is applied to a first electrode pair composing the biosensor;

a second current value measurement means that detects, as a second current value, a current that is generated when a second voltage is applied to a second electrode pair composing the biosensor;

a control means that exerts control so that, over a predetermined period after the introduction of the blood into the biosensor, the first current value measurement means measures the first current value multiple times, with the first voltage being continuously applied to the first electrode pair, and so that after the continuous application of the first voltage, the second current value measurement means measures the second current value, with the second voltage being applied, a conversion means that converts, to blood component amounts, pairs of current values consisting of any one of a plurality of first current values measured by the first current value measurement means and the second current value measured by the second current value measurement means, and a calculation means that calculates the blood component amount for the blood introduced into the biosensor, using a plurality of the blood component amounts converted by the conversion means.

A blood component measurement device according to a thirty-third aspect of the present invention (hereinafter may also be referred to as a "fourth blood component measurement device") is a blood component measurement device that measures a blood component amount using a biosensor in which blood is introduced and then a blood component contained in said blood is subjected to oxidation-reduction using an oxidoreductase, wherein the blood component measurement device includes:

a first current value measurement means that detects, as a first current value, an oxidation-reduction current that is generated by the oxidation-reduction when a first voltage is applied to a first electrode pair composing the biosensor;

a second current value measurement means that detects, as a second current value, a current that is generated when a second voltage is applied to a second electrode pair composing the biosensor;

a control means that exerts control so that within a predetermined period after the introduction of the blood into the biosensor, the second current value measurement means applies the second voltage to the second electrode pair in the form of pulses to measure the second current value multiple times and so that after the application of the second voltage, the first current value measurement means measures the first current value, a conversion means that converts, to blood component amounts, pairs of current values consisting of the first current value measured by the first current value measurement means and any one of a plurality of second current values measured by the second current value measurement means, and a calculation means that calculates the blood component amount for the blood introduced into the biosensor, using a plurality of the blood component amounts converted by the conversion means.

A blood component measurement device according to a thirty-fourth aspect of the present invention is the blood component measurement device according to the above-mentioned thirty-second or thirty-third aspect, wherein the blood component measurement device includes a storage means that contains recorded data, stored per blood in which the blood component amount is known, including a plurality of the blood component amounts converted from the pairs of current values, and the calculation means compares the recorded data with measured data including a plurality of the blood component amounts converted by the conversion means and calculates the blood component amount of the blood from which recorded data most approximated to said measured data was obtained, as the blood component amount of the blood introduced into the biosensor.

A blood component measurement device according to a thirty-fifth aspect of the present invention is the blood component measurement device according to any one of the above-mentioned thirty-second to thirty-fourth aspects, wherein the blood component measurement device includes:

a storage means that contains recorded data, stored per blood in which the blood component amount is known and per ambient temperature, including a plurality of the blood component amounts converted from the pairs of current values, and a temperature detection means that detects the ambient temperature, and the calculation means extracts a plurality of recorded data obtained at a temperature near the ambient temperature detected by the temperature detection means, compares said plurality of recorded data thus extracted with measured data including the plurality of the blood component amounts converted by the conversion means, and calculates the blood component amount of the blood from which recorded data most approximated to said measured data was obtained, as the blood component amount of the blood introduced into the biosensor.

A blood component measurement device according to a thirty-sixth aspect of the present invention is the blood component measurement device according to the above-mentioned thirty-fourth or thirty-fifth, wherein the calculation means compares a plurality of blood component amounts converted from arbitrary combinations of the first current value and the second current value selected from the pairs of current values measured as a result of the control exerted by the control means, with recorded data of a plurality of blood component amounts converted from the same combinations as the arbitrary combinations of the first current value and the second current value stored in the storage means, and calculates the blood component amount of the blood from which recorded data most approximated was obtained, as the blood component amount of the blood introduced into the biosensor.

A blood component measurement method according to a thirty-seventh aspect of the present invention (hereinafter may also be referred to as a "third blood component measurement method") is a blood component measurement method in which a blood component amount is measured using a biosensor in which blood is introduced and then a blood component contained in said blood is subjected to oxidation-reduction using an oxidoreductase, wherein the blood component measurement method includes:

a first current value measurement step for detecting, as a first current value, an oxidation-reduction current that is generated by the oxidation-reduction when a first voltage is applied to a first electrode pair composing the biosensor;

a second current value measurement step for detecting, as a second current value, a current that is generated when a second voltage is applied to a second electrode pair composing the biosensor;

a conversion step for converting, to blood component amounts, pairs of current values consisting of any one of a plurality of first current values measured in the first current value measurement step and the second current value measured in the second current value measurement step; and a calculation step for calculating the blood component amount contained in the blood using a plurality of the blood component amounts converted in the conversion step, wherein in the first current value measurement step, the first current value is measured multiple times over a predetermined period after the introduction of the blood into the biosensor, with the first voltage being continuously applied to the first electrode pair, in the second current value measurement step, the second current value is measured after the first current measurement step, with the second voltage being applied, and in the conversion step, a plurality of blood component amounts are obtained from a plurality of first current values measured in the first current value measurement step and the second current value measured in the second current value measurement step.

A blood component measurement method according to a thirty-eighth aspect of the present invention (hereinafter may also be referred to as a "fourth blood component measurement method") is a blood component measurement method in which a blood component amount is measured using a biosensor in which blood is introduced and then a blood component contained in said blood is subjected to oxidation-reduction using an oxidoreductase, wherein the blood component measurement method includes:

a first current value measurement step for detecting, as a first current value, an oxidation-reduction current that is generated by the oxidation-reduction when a first voltage is applied to a first electrode pair composing the biosensor;

a second current value measurement step for detecting, as a second current value, a current that is generated when a second voltage is applied to a second electrode pair composing the biosensor;

a conversion step for converting, to blood component amounts, pairs of current values consisting of the first current value measured in the first current value measurement step and any one of a plurality of second current values measured in the second current value measurement step; and a calculation step for calculating the blood component amount for the blood introduced into the biosensor, using a plurality of the blood component amounts converted in the conversion step, wherein in the second current value measurement step, the second current value is measured multiple times within a predetermined period after the introduction of the blood into the biosensor, with the second voltage being applied to the second electrode pair in the form of pulses, and in the first current value measurement step, the first current value is measured after the second current value measurement step.

A blood component measurement method according to a thirty-ninth aspect of the present invention is the blood component measurement method of the above-mentioned thirty-seventh or thirty-eighth aspect, wherein the calculation step includes:

referring to recorded data, stored in a storage means per blood in which the blood component amount is known, including a plurality of the blood component amounts converted from the pairs of current values;

comparing the recorded data with measured data including the plurality of the blood component amounts converted in the conversion step; and calculating the blood component amount of the blood from which recorded data most approximated to said measured data was obtained, as the blood component amount of the blood introduced into the biosensor.

A blood component measurement method according to a fortieth aspect of the present invention is the blood component measurement method of any one of the above-mentioned thirty-seventh to thirty-ninth aspects, wherein the blood component measurement method includes a temperature detection step for detecting ambient temperature, and the calculation step includes:

referring to recorded data, stored in a storage means per blood in which the blood component amount is known and per ambient temperature, including the plurality of the blood component amounts converted from the pairs of current values;

extracting a plurality of recorded data obtained at a temperature near the ambient temperature detected in the temperature detection step;

comparing said plurality of recorded data thus extracted with measured data including a plurality of the blood component amounts converted in the conversion step; and calculating the blood component amount of the blood from which recorded data most approximated to said measured data was obtained, as the blood component amount of the blood introduced into the biosensor.

Effects of the Invention

According to the first measurement device, the third measurement device, the first measurement method, and the third measurement method of the present invention, since the blood component amount of the blood introduced into a biosensor is calculated using a plurality of blood component amounts converted from a plurality of first current values and a second current value, the errors in measuring blood components can be suppressed.

Furthermore, according to the second measurement device, the fourth measurement device, the second measurement method, and the fourth measurement method of the present invention, since the blood component amount of the blood introduced into a biosensor is calculated using a plurality of blood component amounts converted from a plurality of second current values and a first current value, the errors in measuring blood components can be suppressed.

BRIEF DESCRIPTION OF DRAWINGS

FIG. 7A shows a voltage change for obtaining the first response values while FIG. 7B shows a voltage change for obtaining the second response value.

DESCRIPTION OF THE INVENTION

Hereinafter, embodiments of the present invention are described with reference to the drawings.

First, a biosensor 1 is described.

Figure 1:
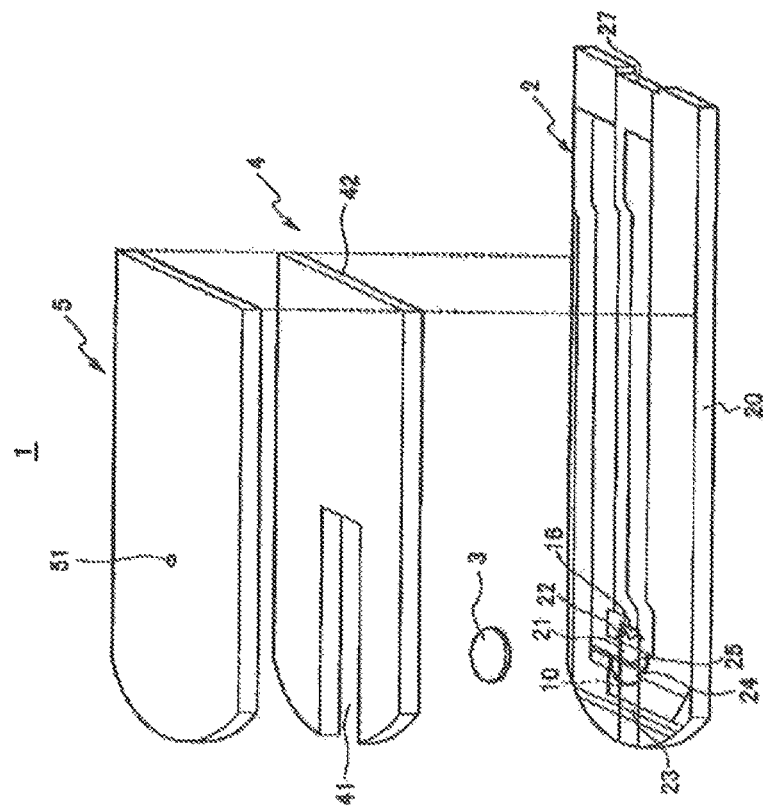
FIG. 1 is an exploded perspective view of a biosensor that can be attached to a measurement device described as an embodiment of the present invention.
Figure 2:
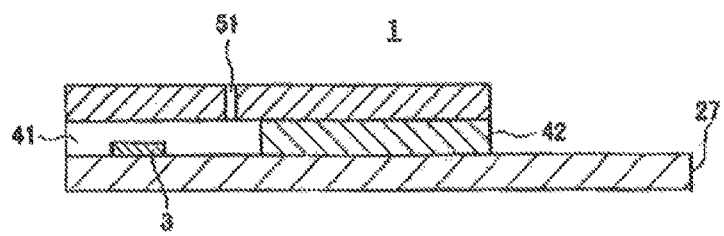
FIG. 2 is a cross-sectional view of the biosensor that can be attached to a measurement device described as an embodiment of the present invention.
Figure 3:
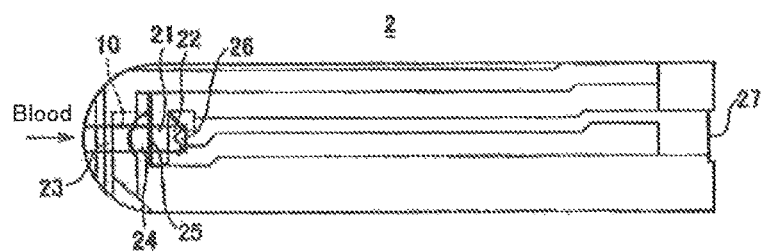
FIG. 3 is a top view of a blood component measurement layer of the biosensor that can be attached to a measurement device described as an embodiment of the present invention.

The biosensor 1 that can be attached to a measurement device described as an embodiment of the present invention includes, for example, such respective parts as shown in FIG. 1 to FIG. 3. FIG. 1 is an exploded perspective view of the biosensor 1. FIG. 2 is a cross-sectional view of the biosensor 1. The biosensor 1 includes a blood component measurement layer 2, a reagent layer 3, a spacer layer 4, and a surface layer 5. The biosensor 1 is formed of these respective layers stacked together. The biosensor 1 is described below using, as an example, a biosensor that measures glucose as a blood cell component but it is not limited thereto.

The biosensor 1 can be attached to or detached from a measurement device 6 described later. The biosensor 1 composes a biosensor system together with the measurement device 6. Using the measurement device 6, the biosensor system measures the amount of a component of the matrix contained in blood spotted as a sample to a sample spotting site 41 located at the tip of the biosensor 1. The measurement device 6 displays, as a measurement result, the blood component amount of the blood introduced into the biosensor 1. In the following description, the phrase "the blood component amount" encompasses a glucose concentration (a first component amount) and/or a blood cell amount (a second component amount).

In order to quantify the blood component amount in the blood using the biosensor 1, first an end 27 of the biosensor 1 is inserted into the measurement device 6 by a user. Then, the measurement device 6 applies voltages to the electrodes of the biosensor 1 described later. In this state, blood is supplied to the sample spotting site 41. When the blood is spotted, said blood is drawn into the biosensor 1. This blood dissolves the reagent layer 3. The measurement device 6 detects an electrical change generated between the electrodes of the biosensor 1 to measure the blood component amount.

In the present embodiment, the biosensor 1 measures the amount of a specific blood component contained in the blood of a human body used as a sample liquid. The amount of the specific blood component is a glucose concentration in the present embodiment. In the following description, disclosure is made regarding the measurement of the glucose concentration contained in the blood of a human body. However, the biosensor system in the present embodiment can also measure lactic acid, cholesterol, or other components when a suitable enzyme is selected.

The blood component measurement layer 2 is configured with a conductive layer formed on an insulating substrate 20 that is formed of, for example, polyethylene terephthalate (PET), polycarbonate (PC), polyimide (PI), polyethylene (PE), polypropylene (PP), polystyrene (PS), polyvinyl chloride (PVC), polyoxymethylene (POM), monomer cast nylon (MC), polybutylene terephthalate (PBT), methacrylic resin (PMMA), ABS resin (ABS), or glass. The conductive layer is formed of an electroconductive material such as carbon or noble metal such as gold, platinum, or palladium, for example. The conductive layer is formed by, for example, a screen printing method or a sputter deposition method. The conductive layer can be formed on the whole surface or at least a part of the substrate. The conductive layer may be coated with a polymeric material for the purpose of preventing impurities from adhering thereto or preventing it from being oxidized. The coating of the surface of the conductive layer can be carried out by, for example, preparing a solution of a polymeric material, dropping or applying it to the surface of the conductive layer, and then drying it. Examples of the drying method include natural drying, air drying, hot air drying, and heat drying.

Furthermore, the size of the insulating substrate 20 is not particularly limited. It has, for example, a total length of 5 to 100 mm, a width of 2 to 50 mm, and a thickness of 0.05 to 2 mm, preferably a total length of 7 to 50 mm, a width of 3 to 20 mm, and a thickness of 0.1 to 1 mm, and further preferably a total length of 10 to 30 mm, a width of 3 to 10 mm, and a thickness of 0.1 to 0.6 mm.

Moreover, the material of the spacer layer 4 is not particularly limited. For example, a similar material to that of the substrate 20 can be used. Furthermore, the size of the spacer layer 4 is not particularly limited. It has, for example, a total length of 5 to 100 mm, a width of 2 to 50 mm, and a thickness of 0.01 to 1 mm, preferably a total length of 7 to 50 mm, a width of 3 to 20 mm, and a thickness of 0.05 to 0.5 mm, and more preferably a total length of 10 to 30 mm, a width of 3 to 10 mm, and a thickness of 0.05 to 0.25 mm. The spacer layer 4 has an I-shaped cutaway portion formed to serve as the sample spotting site 41 for introducing blood.

The surface layer 5 is an insulating substrate provided with an air hole 51 in the central portion thereof. The surface layer 5 is disposed to form one body together with the blood component measurement layer 2, with the spacer layer 4 having the sample spotting site 41 as a cutaway portion being interposed between the surface layer 5 and the blood component measurement layer 2. In order to dispose it to form one body, the surface layer 5, the spacer layer 4, and the blood component measurement layer 2 may be bonded together with an adhesive or may be heat-sealed. Examples of the adhesive that can be used herein include an epoxy adhesive, an acrylic adhesive, a polyurethane adhesive, as well as a thermosetting adhesive (such as a hot-melt adhesive) and a UV curable adhesive.

The material of the surface layer 5 is not particularly limited but, for example, a similar material to that of the substrate 20 can be used. It is further preferable that the portion corresponding to the ceiling portion of the sample spotting site 41 of the surface layer 5 be subjected to a hydrophilic treatment. Examples of the method used for the hydrophilic treatment include a method in which a surfactant is applied and a method in which a hydrophilic functional group such as a hydroxyl group, a carbonyl group, or a carboxyl group is introduced into the surface of the surface layer 5 by, for example, a plasma treatment. The size of the surface layer 5 is not particularly limited but it has, for example, a total length of 5 to 100 mm, a width of 3 to 50 mm, and a thickness of 0.01 to 0.5 mm, preferably a total length of 10 to 50 mm, a width of 3 to 20 mm, a thickness of 0.05 to 0.25 mm, and more preferably a total length of 15 to 30 mm, a width of 5 to 10 mm, and a thickness of 0.05 to 0.1 mm. Preferably, the air hole 51 is formed in the surface layer 5. The shape of the air hole is, for example, round, oval, or polygonal. The air hole 51 has, for example, a maximum diameter of 0.01 to 10 mm, preferably a maximum diameter of 0.05 to 5 mm, and more preferably a maximum diameter of 0.1 to 2 mm.

In the blood component measurement layer 2, as shown in FIG. 3, a plurality of slits are provided for the conductive layer located on the substrate 20 to form various electrodes. FIG. 3 is a top view of the blood component measurement layer 2 in the biosensor 1. In the blood component measurement layer 2, a first electrode pair composed of a first working electrode 21 and a first counter electrode 22 is formed. The first working electrode 21 and the first counter electrode 22 are disposed at positions that contact an oxidoreductase and a mediator of the reagent layer 3 described later. In the blood component measurement layer 2, a second electrode pair composed of a second working electrode 23 and a second counter electrode 24 is formed. The second working electrode 23 is disposed at a position that does not contact the oxidoreductase and the mediator of the reagent layer 3 described later. The second counter electrode 24 is disposed at a position that contacts the oxidoreductase and the mediator of the reagent layer 3 described later but does not contact the first working electrode 21. Furthermore, in the blood component measurement layer 2, a detection electrode 26 for detecting the introduction of blood is formed. These first working electrode 21, first counter electrode 22, second working electrode 23, second counter electrode 24, and detection electrode 26 are electrically connected to the measurement device 6, with the biosensor 1 being inserted in the measurement device 6.

When a first current value that depends on the glucose concentration to a high degree is to be measured, a voltage (a first voltage) is applied between the first working electrode 21 and the first counter electrode 22, with the first working electrode 21 and the first counter electrode 22 being used as a positive electrode and a negative electrode, respectively.

When a second current value that depends on the blood cell amount to a high degree is to be measured, a voltage (a second voltage) is applied in the form of pulses between the second working electrode 23 and the second counter electrode 24, with the second working electrode 23 and the second counter electrode 24 being used as a positive electrode and a negative electrode, respectively. Examples of the form of pulses include forms of a rectangular wave, a triangular wave, etc. The details of such voltage applications are described later.

A non-interference portion 25 with no conductive layer formed thereon may be provided between the first working electrode 21 and the second counter electrode 24. The non-interference portion 25 separates the first working electrode 21 and the second counter electrode 24 from each other. This allows the non-interference portion 25 to prevent a mediator generated in the second counter electrode 24 from flowing into the first working electrode 21 in measuring the second current value. The non-interference portion 25 does not need to be provided when the first voltage and the second voltage are not applied simultaneously.

In the blood component measurement layer 2, an identification section for identifying the biosensor 1 using the measurement device 6 may be formed with electrodes. The identification section has, for example, a shape for identifying the type of the biosensor 1 and the difference in output characteristics per production lot. The identification section is formed, for example, on the side of the end 27 of the biosensor 1 and can be read by the measurement device 6.

As shown in FIG. 1, the spacer layer 4 is disposed to cover the respective electrodes 21 to 24 and 26 located on the substrate 20 of the blood component measurement layer 2. The spacer layer 4 is a substrate 42 in which the rectangular sample spotting site 41 provided at the front edge center is formed. The sample spotting site 41 forms a sample supply path 10 shown in FIG. 3. When blood is spotted on the sample spotting site 41, the blood is drawn towards the air hole 51 of the surface layer 5 to the right in FIGS. 1 to 3 by the capillary phenomenon. Thus, the blood is introduced into the first working electrode 21, the first counter electrode 22, the second working electrode 23, and the second counter electrode 24.

As shown in FIG. 1, the reagent layer 3 is disposed between the blood component measurement layer 2 and the spacer layer 4. The reagent layer 3 is formed through application of a reagent containing, for example, an enzyme, a mediator (an electron acceptor), an amino acid, and sugar alcohol. The reagent layer 3 contacts the first working electrode 21 and the first counter electrode 22 that are exposed through the sample spotting site 41 of the spacer layer 4. Furthermore, the reagent layer 3 selectively contains, as optional components, a polymeric material, an enzyme stabilizer, a crystal homogenizer, etc. Over the blood component measurement layer 2 and the reagent layer 3, the surface layer 5 is disposed while leaving one end of the blood component measurement layer 2 exposed, with the spacer layer 4 being interposed therebetween.

Examples of the oxidoreductase of the reagent layer 3 to be used herein include glucose oxidase, lactate oxidase, cholesterol oxidase, cholesterol esterase, uricase, ascorbate oxidase, bilirubin oxidase, glucose dehydrogenase, lactate dehydrogenase, and lactate dehydrogenase. The amount of the oxidoreductase is, for example, 0.01 to 100 U, preferably 0.05 to 10 U, and more preferably 0.1 to 5 U, per biosensor or per measurement. Among them, the oxidoreductase is preferably glucose oxidase or glucose dehydrogenase.

The mediator (the electron acceptor) of the reagent layer 3 is preferably ferricyanide, more preferably potassium ferricyanide. Examples of mediators other than the ferricyanide that can be used herein include p-benzoquinone and derivatives thereof, phenazine methosulfate, methylene blue, as well as ferrocene and derivatives thereof. The amount of the electron acceptor to be mixed is not particularly limited. It is, for example, 0.1 to 1000 mM, preferably 1 to 500 mM, and more preferably 10 to 200 mM, per measurement or per biosensor.

For example, in order to measure the glucose concentration (a blood component) contained in the blood of a human body, the biosensor 1 of the present embodiment uses glucose oxidase as the oxidoreductase and potassium ferricyanide as the mediator that are carried by the reagent layer 3.

In the reagent layer 3, the oxidoreductase and the mediator are dissolved in the blood used as a sample liquid when the blood is introduced into the sample supply path 10. Then, an enzyme reaction proceeds between the glucose, which is a matrix in the blood, and the oxidoreductase and the mediator, and thereby the mediator is reduced to produce ferrocyanide (potassium ferrocyanide in the case of the present embodiment). After completion of this reaction, the mediator thus reduced is electrochemically oxidized, and from the current (a first current value) obtained thereby, a response value (a first response value (mV)) that depends on the glucose concentration in the blood to a high degree is measured.

In the present invention, the blood cells denote red blood cells, white blood cells, platelets, and combinations thereof, which are contained in the blood, but preferably the blood cells denote red blood cells. Furthermore, in the present invention, the amount of the blood cells denotes, for example, the ratio (volume ratio) of the red blood cells contained in the blood, preferably the hematocrit (Hct) value.

Next, the configuration of the measurement device 6 is described.

Figure 4:
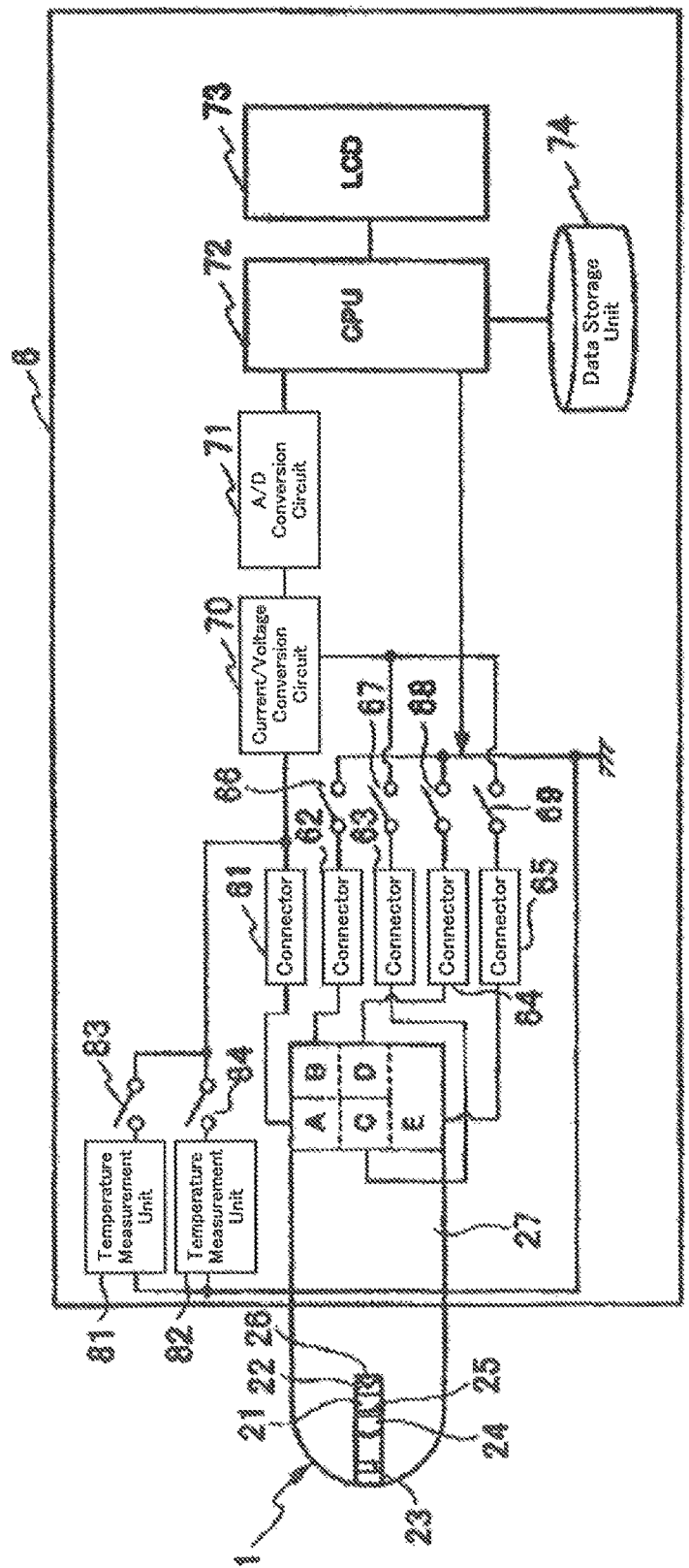
FIG. 4 is a block diagram showing the configuration of a measurement device described as an embodiment of the present invention.

The measurement device 6 carries out measurement using the biosensor 1 in which blood is introduced and a blood component contained in said blood is subjected to oxidation-reduction using the oxidoreductase. As shown in FIG. 4, the measurement device 6 is connected to electrodes A to E provided at the end 27 of the biosensor 1, with the biosensor 1 being inserted in the measurement device 6. The electrode A corresponds to the first working electrode 21, the electrode B corresponds to the first counter electrode 22, the electrode C corresponds to the second working electrode 23, the electrode D corresponds to the second counter electrode 24, and the electrode E corresponds to the detection electrode 26.

The measurement device 6 includes a plurality of connectors 61 to 65 and switches 66 to 69, a current/voltage conversion circuit 70, an A/D conversion circuit 71, a CPU 72, an LCD 73, and a data storage unit 74 (a storage means). Furthermore, the measurement device 6 includes temperature measurement units 81, 82 (temperature detection means) for measuring the device inner temperature and switches 83, 84 for said temperature measurement units 81, 82. The connectors 62, 64 connected to the first counter electrode 22 and the second counter electrode 24 that serve as negative electrodes and the switches 67, 68 are grounded.

The temperature measurement unit 81 and the temperature measurement unit 82 each measure the temperature inside the measurement device 6 as the ambient temperature of the blood introduced therein. It is desirable that the temperature measurement units 81, 82 each measure the temperature of, for example, a position near the biosensor 1 inserted into the measurement device 6. The temperature measurement values measured by the temperature measurement units 81, 82 are supplied to the CPU 72. The CPU 72 compares the two temperature measurement results. When the difference between the temperatures is not within a predetermined threshold, it is determined that one of the temperature measurement units 81, 82 is not working. This allows the measurement device 6 to detect failures accurately and easily. Furthermore, measurement errors caused by irregular temperature measurements are avoided. The temperature measurement timing may be immediately after the introduction of blood is detected by the detection electrode 26 or when the temperature of the blood introduced into the biosensor 1 is stabilized.

The respective connectors 61 to 65 are connected to the electrodes A to E of the biosensor 1, respectively. The respective switches 66 to 69 are connected to the connectors 62 to 65, respectively. The on/off states of the switches 66 to 69 are controlled by the CPU 72. When the first current value is to be measured, the switch 66 is turned on to apply a voltage between the electrode A connected to the first working electrode 21 and the electrode B connected to the first counter electrode 22. When the second current value is to be measured, the switches 67, 68 are turned on to apply a voltage between the electrode C connected to the second working electrode 23 and the electrode D connected to the second counter electrode 24. The voltage to be applied between the first working electrode 21 and the first counter electrode 22 as well as the voltage to be applied between the second working electrode 23 and the second counter electrode 24 can be changed. When the introduction of blood is to be detected, the switch 69 is turned on to apply a voltage to the electrode E connected to the detection electrode 26.

The current/voltage conversion circuit 70 is connected to the connectors 61 to 65 and the temperature measurement units 81, 82. The first current value and the second current value of the currents flowing between the first working electrode 21, the second working electrode 23, and the other electrodes are supplied to the current/voltage conversion circuit 70. Furthermore, currents corresponding to the ambient temperatures measured by the temperature measurement units 81, 82 are supplied to the current/voltage conversion circuit 70. The current/voltage conversion circuit 70 converts the first current value and the second current value supplied thereto to voltages. The voltage values thus converted are supplied to the A/D conversion circuit 71.

The A/D conversion circuit 71 is supplied with voltage values from the current/voltage conversion circuit 70. The A/D conversion circuit 71 converts the voltage values thus supplied thereto to pulsed digital data and then outputs them to the CPU 72.

The CPU 72 controls respective parts included in the measurement device 6. The CPU 72 exerts control for turning the respective switches 66 to 69 on or off. Furthermore, the CPU 72 calculates the first response value [mV] corresponding to the first current value and the second response value [mV] corresponding to the second current value based on the digital data supplied from the A/D conversion circuit 71. The CPU 72 converts, to a blood component amount, a pair of the first response value and the second response value (a conversion means). Furthermore, the CPU 72 calculates the blood component amount for the blood introduced into the biosensor 1 using a plurality of blood component amounts that were converted (a calculation means). The process for converting the first response value and the second response value to the blood component amount and then calculating the blood component amount of the blood introduced into the biosensor 1 is described later.

The LCD 73 is an LCD (a liquid crystal display; an output unit) that displays the measurement values calculated by the CPU 72.

The data storage unit 74 contains data stored therein that can be referred to by the CPU 72. The data storage unit 74 contains recorded data stored therein that are used for calculating the blood component amount (at least the glucose concentration) by the CPU 72. The recorded data includes a plurality of blood component amounts that were converted from pairs of any one of a plurality of first current values and a second current value, per blood in which the blood component amount is known.

The data storage unit 74 may contain recorded data recorded per blood in which the blood component amount is known and per ambient temperature. The recorded data includes a plurality of blood component amounts that were converted from pairs of any one of a plurality of first current values and a second current value.

The data storage unit 74 may contain stored data, stored per blood in which the blood component amount is known, including a plurality of blood component amounts that were converted from arbitrary combinations of a plurality of first response values and a plurality of second response values. Furthermore, the data storage unit 74 may contain stored data, stored per blood in which the blood component amount is known and per ambient temperature, including a plurality of blood component amounts that were converted from arbitrary combinations of a plurality of first response values and a plurality of second response values. In this case, the CPU 72 uses the same combinations of first response values and second response values as the arbitrary combinations included in the stored data to be converted to a plurality of blood component amounts and then calculates the blood component amount of the blood introduced into the biosensor 1. As described later, a predetermined period denotes a duration set for measuring the blood component amount (the first component amount and/or the second component amount).

Next, basic operations of the above-mentioned measurement device 6 are described.

In the measurement device 6, when a blood component amount is to be measured, first the introduction of blood is detected by the detection electrode 26.

When measuring the first current value, the measurement device 6 allows the CPU 72 to turn on the switch 66 to apply a voltage (the first voltage) between the first working electrode 21 and the first counter electrode 22 (the first electrode pair). In this state, the CPU 72 measures the oxidation-reduction current (the first current value) that is generated by oxidation-reduction (a first current value measurement means, a first current value measurement step). Furthermore, when measuring the second current value, the measurement device 6 allows the CPU 72 to turn on the switches 67, 68 to apply a voltage (the second voltage) between the second working electrode 23 and the second counter electrode 24 (the second electrode pair). In this state, the CPU 72 measures the current (the second current value) that is generated when the voltage is applied to the second working electrode 23 and the second counter electrode 24 (a second current value measurement means, a second current value measurement step). The CPU 72 obtains the first current value as the first response value and the second current value as the second response value.

The measurement device 6 converts a pair of a first response value and a second response value to a blood component amount using a conversion matrix. In this case, the measurement device 6 converts pairs of any one of a plurality of first current values and a second current value to a plurality of blood component amounts (a conversion means, a conversion step). The measurement device 6 obtains the blood component amount of the blood introduced into the biosensor 1 based on the plurality of blood component amounts (a calculation means, a calculation step). The process for conversion to blood component amounts and the process for calculating the blood component amount are described later.

The CPU 72 measures the first current value and the second current value within a predetermined period after the introduction of blood into the biosensor 1 to obtain the first response value and the second response value. The predetermined period can be set to be a certain period such as five seconds or seven seconds. Furthermore, in the first measurement device, the third measurement device, the first measurement method, or the third measurement method, the CPU 72 exerts control so that the first current value is measured multiple times within a predetermined period, with the first voltage being continuously applied, and the second current value is measured (a control means). The second current value may be measured only once. Furthermore, in the second measurement device, the fourth measurement device, the second measurement method, or the fourth measurement method, the CPU 72 exerts control so that the second current value is measured multiple times within a predetermined period and the first current value is measured (a control means). The first current value may be measured only once. Therefore, the CPU 72 may control the switches 66 to 68 to be turned on or off with respect to measurement timings. Furthermore, the CPU 72 may control the timing at which digital data is obtained by the A/D conversion circuit 71.

In the first measurement device, the third measurement device, the first measurement method, or the third measurement method, the CPU 72 obtains a plurality of first response values and a plurality of second response values from a plurality of first current values and a second current value. The CPU 72 converts a pair of any one of the plurality of first response values and a second response value to a blood component amount using a conversion matrix. The CPU 72 combines a different first response value and the second response value and converts each combination to a blood component amount. Thus, the CPU 72 obtains a plurality of blood component amounts.

In the second measurement device, the fourth measurement device, the second measurement method, or the fourth measurement method, the CPU 72 obtains a plurality of first response values and a plurality of second response values from a first current value and a plurality of second current values. The CPU 72 converts a pair of any one of the plurality of second response values and a first response value to a blood component amount using a conversion matrix. The CPU 72 combines a different second response value and the first response value and converts each combination to a blood component amount. Thus, the CPU 72 obtains a plurality of blood component amounts.

The CPU 72 calculates the blood component amount (at least one of the first component amount and the second component amount) of the blood introduced into the biosensor 1 from the plurality of blood component amounts that were converted (a calculation means). In this case, the CPU 72 may refer to the recorded data stored in the data storage unit 74. The CPU 72 that serves as a calculation means compares a plurality of recorded data including a plurality of blood component amounts stored in the data storage unit 74 with measured data including a plurality of blood component amounts that were converted according to a conversion matrix. Then, the CPU 72 calculates the blood component amount of the blood from which the recorded data most approximated to the measured data was obtained, as the blood component amount of the blood introduced into the biosensor 1.

Furthermore, the measurement device 6 measures ambient temperature with the temperature measurement units 81, 82 when the data storage unit 74 contains recorded data stored per blood in which the blood component amount is known and per ambient temperature. Then, the CPU 72 extracts a plurality of recorded data obtained at a temperature near the ambient temperatures detected by the temperature measurement units 81, 82. The CPU 72 compares said plurality of recorded data thus extracted with measured data including a plurality of blood component amounts that were converted. The CPU 72 calculates the blood component amount of the blood from which the recorded data most approximated to said measured data was obtained, as the blood component amount of the blood introduced into the biosensor 1.

Moreover, in the measurement device 6, the data storage unit 74 contains a plurality of blood component amounts, stored as the recorded data, converted from arbitrary combinations of a first response value and a second response value. In this case, the measurement device 6 obtains measured data including a plurality of blood component amounts converted from the same combinations of a first response value and a second response value as the combinations in said recorded data. Then, the measurement device 6 compares the recorded data of the plurality of blood component amounts obtained from arbitrary combinations of response values with measured data of the plurality of blood component amounts converted from the same combinations of response values. Thereby, the measurement device 6 can calculate the blood component amount of the blood from which the recorded data most approximated to said measured data was obtained, as the blood component amount of the blood introduced into the biosensor 1.

Next, in the first measurement device, the third measurement device, the first measurement method, or the third measurement method, an operation of calculating the blood component amount from a combination of any one of a plurality of first response values and a second response value using a conversion matrix in the measurement device 6 as described above is described. In the second measurement device, the fourth measurement device, the second measurement method, or the fourth measurement method, an operation of calculating the blood component amount from a combination of any one of a plurality of second response values and a first response value using a conversion matrix in the measurement device 6 as described above is described.

Figures 5, 6:
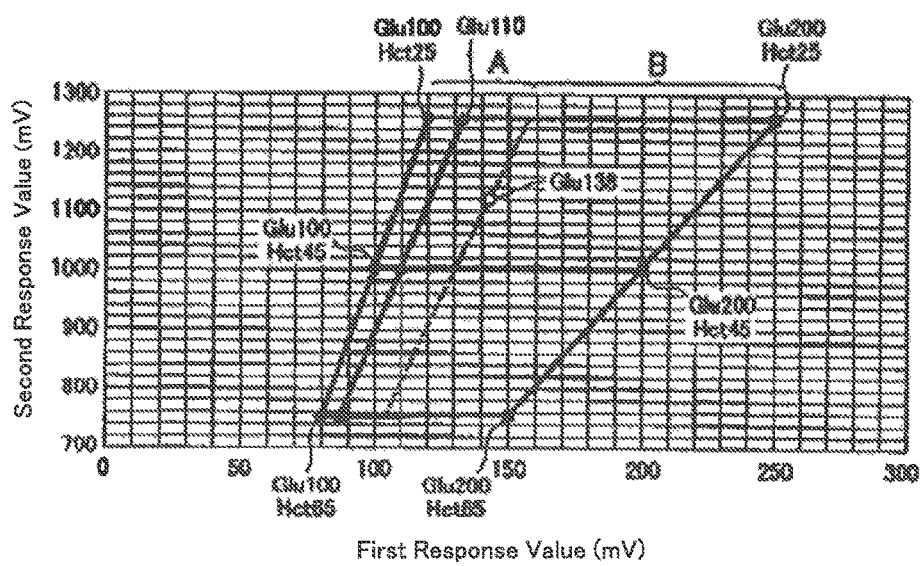
FIG. 5 is a table showing first response values and second response values with respect to known glucose concentrations and blood cell amounts.
FIG. 6 is a graph showing the relationship between the first response value and the second response value with respect to the known glucose concentrations and blood cell amounts.

In the measurement device 6, the first response value of the measurement device 6 that is expected to be supplied to the CPU 72 is, for example, as shown in FIG. 5. For example, when the glucose concentration is 100 mg/dl and the blood cell amount (Hct) is 25%, the CPU 72 is expected to obtain a first response value of 120 as a current value and a second response value of 1250 as a current value. Such expected values of the first response value and the second response value can be obtained by preparing blood in which the glucose concentration and the blood cell amount have been regulated beforehand, and then carrying out measurement with the biosensor 1 and the measurement device 6.

When the first response values and the second response values, each of which was obtained from blood with a known glucose concentration and blood cell amount shown in FIG. 5, are plotted and lines connecting such points thus plotted are drawn, a conversion matrix as shown in FIG. 6 can be created. This conversion matrix shows that the first response value changes when bloods have different blood cell amounts even when having the same glucose concentration.

In the conversion matrix, the first response values and the second response values that are plotted on the line connecting the points obtained from the same known glucose concentrations can be converted to said known glucose concentrations and blood cell amounts. Therefore, using the conversion matrix, the glucose concentration and the blood cell amount can be obtained from the first response value and the second response value obtained from unknown blood. For example, when the first response value and the second response value indicated with a white circle in FIG. 6 were obtained, the ratio (A:B) between 100 mg/dl and 200 mg/dl of the first response values in the conversion matrix is taken. Thereby, a glucose concentration of 138 mg/dl can be obtained. Similarly, the ratio between 25 and 45 of the second response values in the conversion matrix is taken, and thereby the unknown blood cell amount can be determined.

As described above, with the conversion matrix prepared beforehand, a pair of the first response value and the second response value can be converted to the glucose concentration and the blood cell amount as the first component amount and the second component amount (the blood component amount).

Similarly, in the conversion matrix, the second response values plotted on the line connecting the points obtained from the same known blood cell amounts can be converted to said known blood cell amounts. Therefore, using the conversion matrix, the glucose concentration and the blood cell amount can be obtained from the first response value and the second response value obtained from unknown blood.

As described above, with the conversion matrix being prepared beforehand, the glucose concentration and the blood cell amount (the blood component amount) can be obtained from a pair of the first response value and the second response value.

Next, it is described that in the first or third measurement device 6 as described above, recorded data is compared with measured data and thereby the blood component amount of the blood introduced into the biosensor 1 can be calculated.

Figure 9:
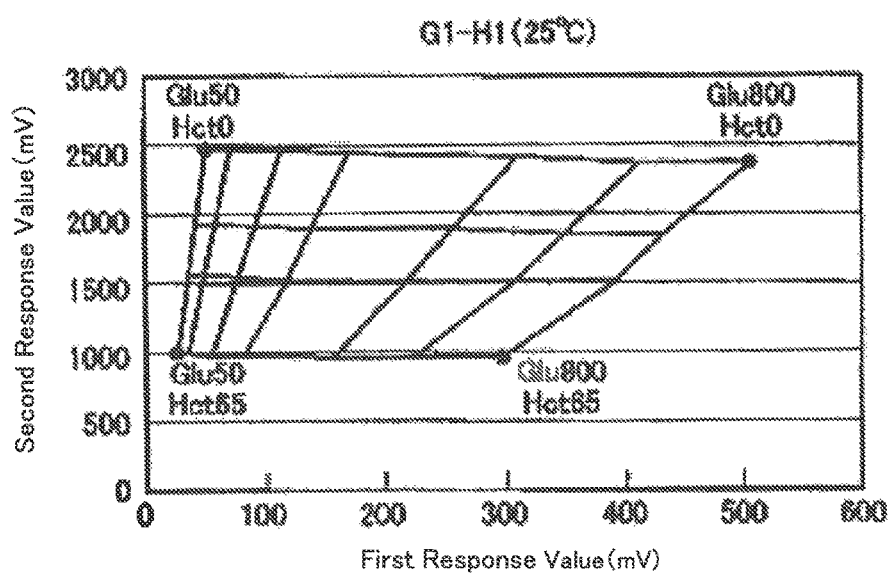
FIG. 9 is a graph showing a conversion matrix that is used by a measurement device described as an embodiment of the present invention.
Figure 10:
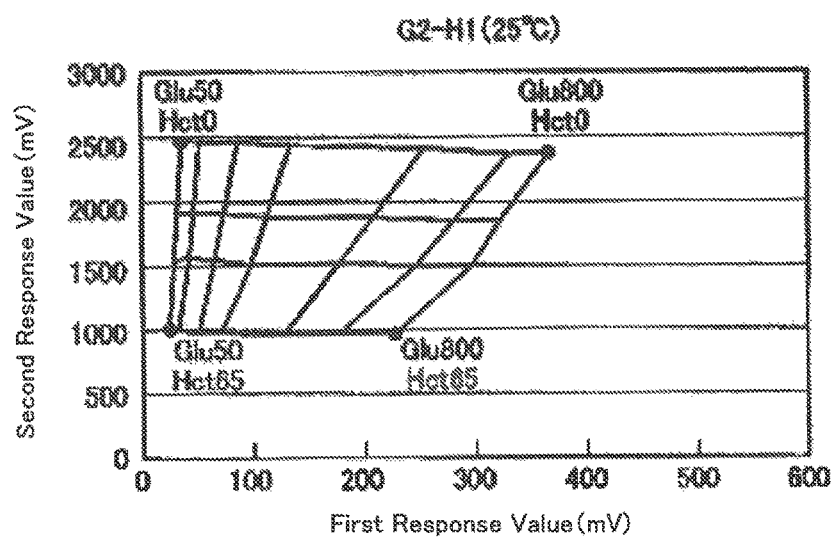
FIG. 10 is a graph showing another conversion matrix that is used by a measurement device described as an embodiment of the present invention.
Figure 11:
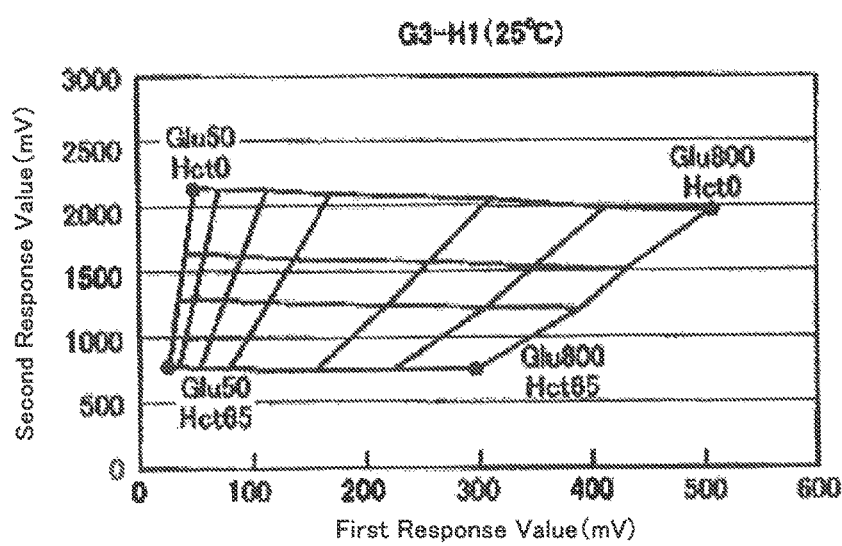
FIG. 11 is a graph showing another conversion matrix that is used by a measurement device described as an embodiment of the present invention.

The first or third measurement device 6 described as the present embodiment obtains a plurality of first response values and one second response value by operations as described with reference to FIGS. 7 and 8, for example. Then, the first or third measurement device 6 refers to conversion matrices as shown in FIGS. 9 to 11 and can convert a pair of any one of the plurality of first response values and the second response value to a blood component amount.

Figure 7A:
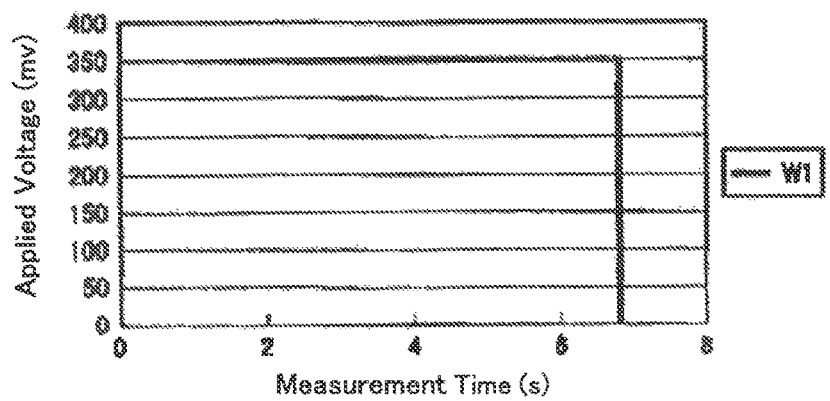
FIGS. 7A and 7B each are a graph showing an operation of applying a voltage to a biosensor by a measurement device described as an embodiment of the present invention.

The first or third measurement device 6 applies a first voltage as shown in FIG. 7A between the first working electrode 21 and the first counter electrode 22 to measure the first current value. The CPU 72 applies, as the first voltage, for example, a voltage of 350 mV between the first working electrode 21 and the first counter electrode 22. As shown in FIG. 7A, the first voltage is applied continuously over a predetermined period. The predetermined period is from zero second to seven seconds, as an example thereof.

Figure 7B:
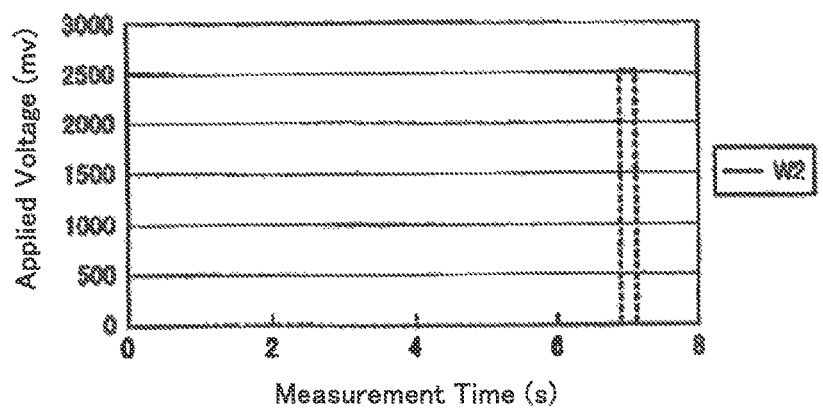

The first or third measurement device 6 applies a second voltage as shown in FIG. 7B between the second working electrode 23 and the second counter electrode 24 to measure the second current value. The CPU 72 applies, for example, a voltage of 2500 mV between the second working electrode 23 and the second counter electrode 24. As shown in FIG. 7B, the second voltage is applied in the late stage of the predetermined period.

Figure 8:
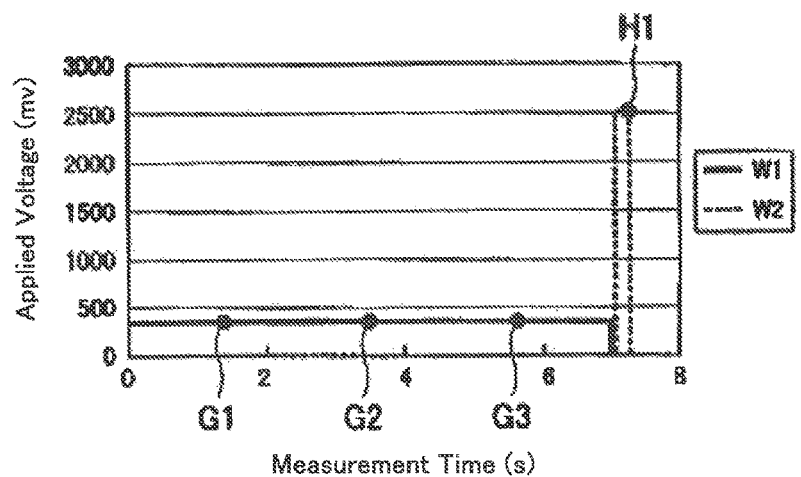
FIG. 8 is a graph showing timings at which the first response values and the second response value are measured by a measurement device described as an embodiment of the present invention.

The CPU 72 applies both the first voltage and the second voltage shown in FIGS. 7A and 7B to the biosensor 1 to measures the first current values and the second current value at the timings as shown in FIG. 8 and thereby obtains the first response values and the second response value. In this example, the CPU 72 obtains first response values G1, G2, G3 over three times, in the first half, the middle, and the second half, during the predetermined period. It is desirable that the CPU 72 obtain the first response value twice, once in a first period included in the first half of the predetermined period and once in a second period included in the second half of the predetermined period. As a result, the CPU 72 can obtain at least the first response value G1 and the first response value G3. The CPU 72 obtains the second response value in the late stage of the predetermined period. As a result, the CPU 72 can obtain a second response value H1. The timing at which the second response value H1 is obtained may be during the application of the first voltage or after the application was stopped.

It is desirable that a period in which the temperature of the blood introduced into the biosensor 1 changes greatly be set as the first period. In the example shown in FIG. 8, a period within two seconds from the measurement start is set as the first period. Furthermore, it is desirable that a period in which the temperature of the blood introduced into the biosensor 1 is stable be set as the second period. In the example shown in FIG. 8, a period between five and seven seconds after the measurement is set as the second period.

As described above, the first or third measurement device 6 applies the first voltage to the first working electrode 21 and the first counter electrode 22 that serve as the first electrode pair during the predetermined period to measure the first current value (the oxidation-reduction current) multiple times at predetermined measurement timings. On the other hand, the first or third measurement device 6 applies the second voltage within the range of a predetermined short period from the predetermined measurement timing. Furthermore, the first or third measurement device 6 applies the second voltage in the form of pulses to the second working electrode 23 and the second counter electrode 24 that serve as the second electrode pair only at the predetermined measurement timing during the predetermined period to measure the second current value.

After the three first response values G1, G2, G3 and one second response value H1 are measured, the CPU 72 refers to three conversion matrices to convert them to three blood component amounts. In this case, the three conversion matrices each are prepared beforehand for each of the combinations of the first response value G1 and the second response value H1, the first response value G2 and the second response value H1, as well as the first response value G3 and the second response value H1.

The CPU 72 converts the first response value G1 and the second response value H1 to a blood component amount using the conversion matrix G1-H1 shown in FIG. 9. Similarly, the CPU 72 converts the first response value G2 and the second response value H1 to a blood component amount using the conversion matrix G2-H1 shown in FIG. 10. Similarly, the CPU 72 converts the first response value G3 and the second response value H1 to a blood component amount using the conversion matrix G3-H1 shown in FIG. 11.

Specifically, the first or third measurement device 6 contains such conversion matrices as those shown in FIGS. 9 to 11 stored in the data storage unit 74. The first or third measurement device 6 measures a plurality of first response values G1 to G3 and a second response value H1 with respect to an unknown blood to obtain a pair of G1 and H1, a pair of G2 and H1, and a pair of G3 and H1. Then, the first or third measurement device 6 plots a point determined by the combination of a first response value and the second response value on each conversion matrix and converts said first response value and second response value to a blood component amount using each conversion matrix. Accordingly, the first or third measurement device 6 can obtain the blood component amount with respect to each of the combination of G1 and H1, the combination of G2 and H1, and the combination of G3 and H1.

Next, the first or third measurement device 6 compares recorded data including three blood component amounts for the respective pairs of the plurality of first response values and the second response value described above, with the three blood component amounts that are used as measured data. As a result of the comparison, the first or third measurement device 6 can extract the recorded data closest to the measured data. The first or third measurement device 6 can calculate the blood component amount of the blood from which the recorded data thus extracted was obtained, as the blood component amount of the blood introduced into the biosensor 1.

Figures 12, 13, 14:
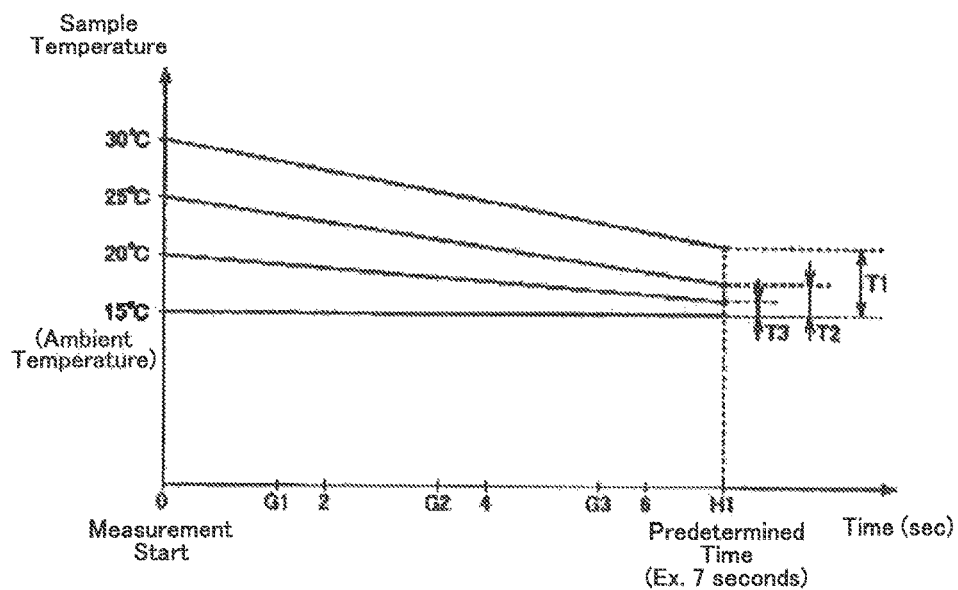
FIG. 12 is a graph showing the temperature change that occurs after the introduction of blood into a biosensor described as an embodiment of the present invention.
FIG. 13 is a table showing the relationships among ambient temperatures, sample introduction temperatures, and blood component amounts that were converted, in a measurement device described as an embodiment of the present invention.
FIG. 14 is a table showing the relationship between first response values and a second response value and the blood component amounts that were converted, per temperature, in a measurement device described as an embodiment of the present invention.

As shown in FIG. 12, the temperature of the blood that is used as a sample introduced into the biosensor 1 decreases according to the elapsed time after the introduction into the biosensor 1. As described above, when the measurement time (the predetermined time) for the blood component amount is set to be seven seconds, how the temperature decreases during the measurement time differs according to the blood temperature measured at the time of the introduction into the biosensor 1. The higher the blood temperature is at the time of the introduction into the biosensor 1, the steeper the slope of the decrease in blood temperature becomes. Furthermore, the blood temperature at the end of the measurement time differs according to the blood temperature measured at the time of the introduction into the biosensor 1. The higher the blood temperature is at the time of the introduction into the biosensor 1, the bigger the difference from the ambient temperature is at the end of the measurement time. For example, when blood with a temperature of 30° C. is introduced into the biosensor 1, the difference in temperature between the blood temperature and the ambient temperature is T1 at the end of the measurement time. Furthermore, when blood with a temperature of 25° C. is introduced into the biosensor 1, the difference in temperature between the blood temperature and the ambient temperature is T2 at the end of the measurement time. When blood with a temperature of 20° C. is introduced into the biosensor 1, the difference in temperature between the blood temperature and the ambient temperature is T3 at the end of the measurement time.

Since the first response values and the second response value measured by the first or third measurement device 6 depend on the blood temperature, even when the first response value and the second response value are measured only at the end of the measurement time, accurate first response value and second response value cannot be obtained. Therefore, the first or third measurement device 6 measures the first response value multiple times and the second response value only once during the predetermined measurement time. Moreover, the first or third measurement device 6 combines the first response values and the second response value arbitrarily and obtains a blood component amount per said arbitrary combination.

The first or third measurement device 6 contains recorded data, for example, as shown in FIG. 13 stored in the data storage unit 74. The recorded data includes, as an example, a plurality of blood component amounts obtained from blood, in which the glucose concentration (the first component amount) is 100 mg/dl and the blood cell amount (the second component amount) is 25%, stored per ambient temperature and sample introduction temperature. The sample introduction temperature does not need to be included in the recorded data. Specifically, in the recorded data, an ambient temperature A, a blood component amount Aa1, a blood component amount Aa2, and a blood component amount Aa3 are mapped. The blood component amount Aa1 was converted using the conversion matrix G1-H1 shown in FIG. 9. The blood component amount Aa2 was converted using the conversion matrix G2-H1 shown in FIG. 10. The blood component amount Aa3 was converted using the conversion matrix G3-H1 shown in FIG. 11. It is desirable that the recorded data include the blood component amounts stored for each of a plurality of sample introduction temperatures with respect to the ambient temperature. Furthermore, it is desirable that the recorded data include the blood component amounts stored for each of a plurality of ambient temperatures.

The first or third measurement device 6 compares a plurality of blood component amounts, each of which was converted per combination of any one of a plurality of first response values and a second response value, with a plurality of blood component amounts included in the recorded data and thereby can determine the recorded data most approximated. Specifically, when the ambient temperature is near A, the first or third measurement device 6 extracts the blood component amounts Aa1 to Aa3, Ab1 to Ab3, and Ac1 to Ac3 of respective combinations corresponding to the ambient temperature A. The first or third measurement device 6 compares the blood component amounts of respective combinations that are used as the measured data with the blood component amounts Aa1 to Aa3, Ab1 to Ab3, and Ac1 to Ac3 included in the recorded data that were extracted. The first or third measurement device 6 can calculate the glucose concentration of the blood introduced into the biosensor 1 to be 100 mg/dl, when a plurality of blood component amounts included in the measured data are approximated to the blood component amounts Aa1 to Aa3, Ab1 to Ab3, and Ac1 to Ac3 included in the recorded data.

As described above, the first or third measurement device 6 can calculate the blood component amount of the blood introduced into the biosensor 1 using a plurality of first response values and one second response value that were measured. Thus, the biosensor system can suppress the errors in measuring the blood component amount.

The first response values and the second response value that are used as the measured data vary depending on the ambient temperature of the biosensor 1. For example, assume that the conversion matrices shown in FIGS. 9 to 11 each were obtained at an environmental temperature of 25° C. As shown in FIG. 14, when blood with a glucose concentration of 125 mg/dl is measured, with the ambient temperature of the biosensor 1 being 25° C., and the first response values G1, G2, G3 and the second response value H1 are converted, the glucose concentrations obtained thereby are 125 mg/dl in all combinations. However, when the ambient temperature of the biosensor 1 is 35° C., the values of glucose concentrations are different in all the combinations.

Furthermore, it is described that in the second or fourth measurement device 6 as described above, recorded data is compared with measured data and thereby the blood component amount of the blood introduced into the biosensor 1 can be calculated.

Figure 17:
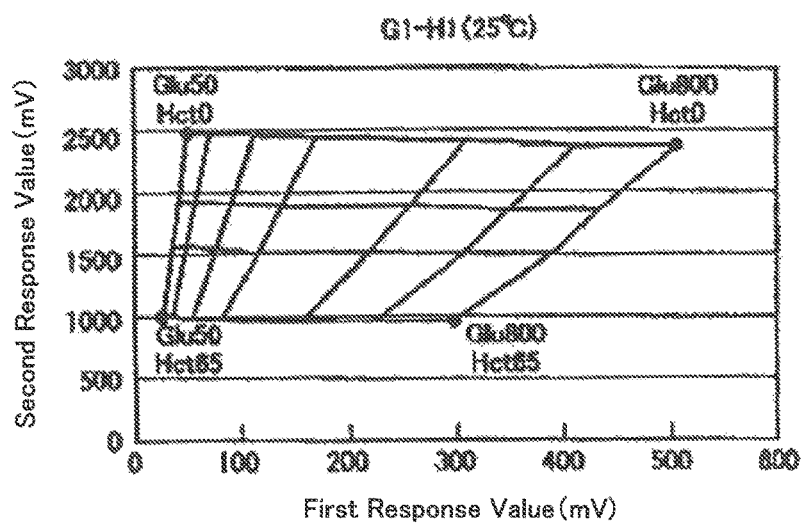
FIG. 17 is a graph showing a conversion matrix that is used by a measurement device described as another embodiment of the present invention.
Figure 18:
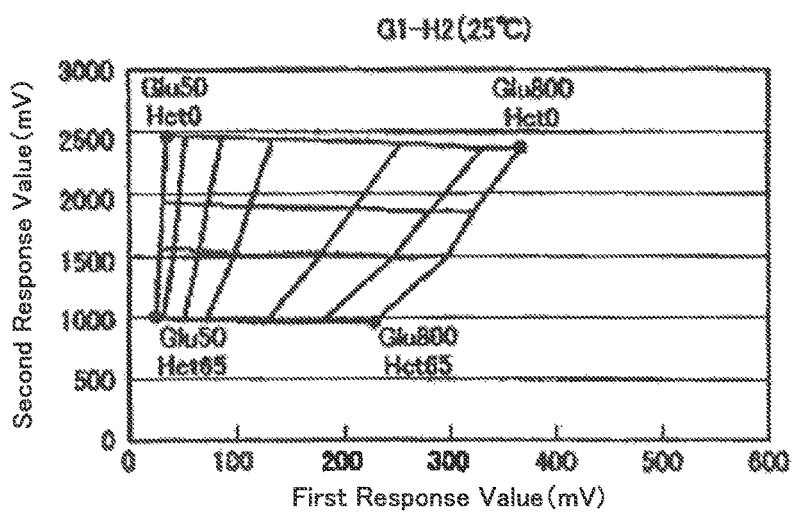
FIG. 18 is a graph showing another conversion matrix that is used by a measurement device described as another embodiment of the present invention.
Figure 19:
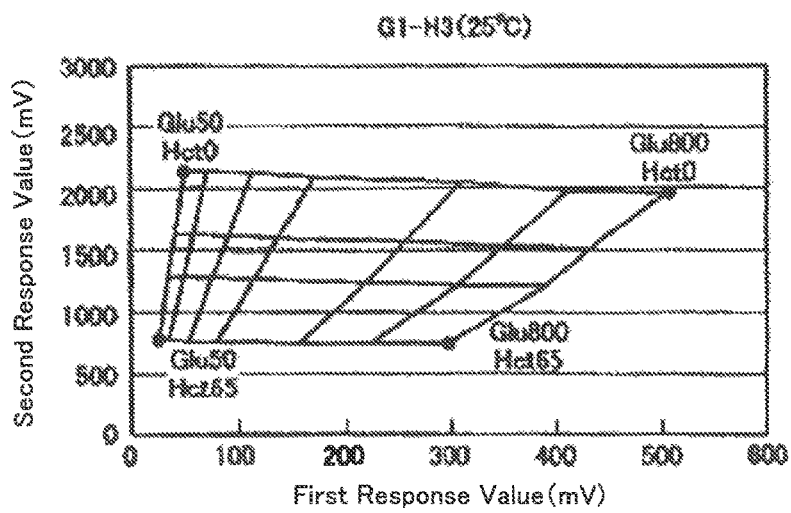
FIG. 19 is a graph showing another conversion matrix that is used by a measurement device described as another embodiment of the present invention.

The second or fourth measurement device 6 described as the present embodiment obtains a plurality of second response values and one first response value by operations as described with reference to FIGS. 15 and 16, for example. Then, the second or fourth measurement device 6 refers to conversion matrices as shown in FIGS. 17 to 19 and can convert a pair of any one of the plurality of second response values and the first response value to a blood component amount.

Figure 15A:
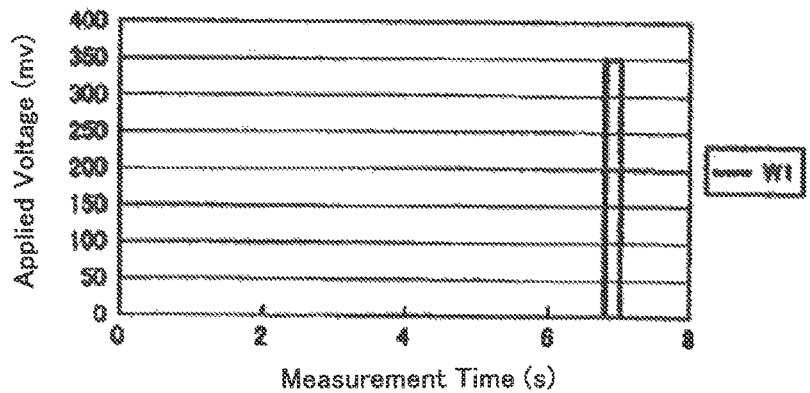
FIGS. 15A and 15B each are a graph showing an operation of applying a voltage to a biosensor by a measurement device described as another embodiment of the present invention, and 15A shows a voltage change for obtaining a first response value while 15B shows voltage changes for obtaining second response values.

The second or fourth measurement device 6 applies a first voltage as shown in FIG. 15A between the first working electrode 21 and the first counter electrode 22 to measure the first current value. The CPU 72 applies, as the first voltage, for example, a voltage of 350 mV between the first working electrode 21 and the first counter electrode 22. As shown in FIG. 15A, the first voltage is applied only once in the form of pulses at the end of a predetermined period. Furthermore, the first voltage may be applied continuously over the predetermined period. The predetermined period is zero second to seven seconds, as an example thereof.

Figure 15B:
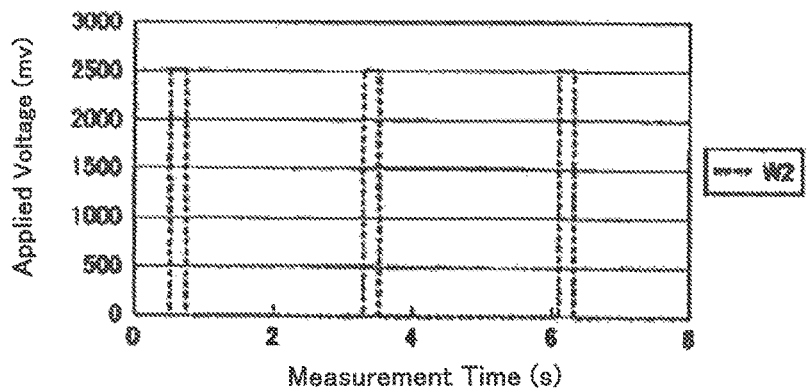

The second or fourth measurement device 6 applies a second voltage as shown in FIG. 15B between the second working electrode 23 and the second counter electrode 24 to measure the second current value. The CPU 72 applies, for example, a voltage of 2500 mV between the second working electrode 23 and the second counter electrode 24. As shown in FIG. 15B, the second voltage is applied three times, in the early, middle, and late stages (in the first half, the middle, and the second half), during the predetermined period. That is, the CPU 72 exerts control so that the second voltage is applied multiple times to the second working electrode 23 and the counter electrode 24 for the blood cell amount in the form of pulses during the predetermined period. Thus, the second response value is measured at each timing at which the second voltage is applied.

Figure 16:
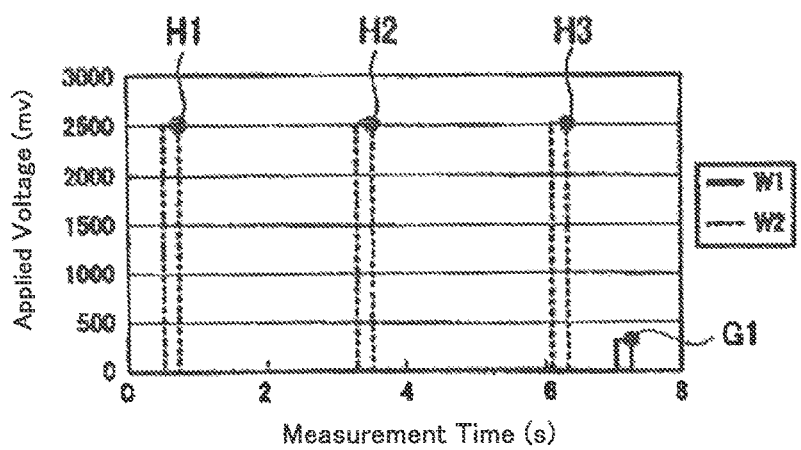
FIG. 16 is a graph showing timings at which the first response value and the second response values are measured by a measurement device described as another embodiment of the present invention.

The CPU 72 applies both the first voltage and the second voltage shown in FIGS. 15A and 15B to the biosensor 1 to obtain the first response value and the second response values at the timings as shown in FIG. 16. In this example, the CPU 72 obtains second response values H1, H2, H3 over three times, in the first half, the middle, and the second half, during the predetermined period. It is desirable that the CPU 72 obtain the second response value at least twice, once in a first period included in the first half of the predetermined period and once in a second period included in the second half of the predetermined period. As a result, the CPU 72 can obtain at least the second response value H1 and the second response value H3. The CPU 72 obtains the first response value in the late stage of the predetermined period. As a result, the CPU 72 can obtain a first response value G1.

It is desirable that a period in which the temperature of the blood introduced into the biosensor 1 changes greatly be set as the first period. In the example shown in FIG. 16, a period within two seconds from the measurement start is set as the first period. Furthermore, it is desirable that a period in which the temperature of the blood introduced into the biosensor 1 is stable be set as the second period. In the example shown in FIG. 16, a period between five and seven seconds after the measurement is set as the second period.

Furthermore, the CPU 72 may exert control so that the second voltage is applied to the second working electrode 23 and the counter electrode 24 for the blood cell amount continuously during the predetermined period. In this case, the CPU 72 measures the second response value at least at two timings, once in the first half and once in the second half, during the predetermined period.

As described above, the second or fourth measurement device 6 applies the second voltage to the second working electrode 23 and the second counter electrode 24 that serve as the second electrode pair during the predetermined period to measure the second current value multiple times at predetermined measurement timings. On the other hand, the second or fourth measurement device 6 applies the first voltage within the range of a predetermined short period from the predetermined measurement timing for the first current value. Furthermore, the second or fourth measurement device 6 applies the first voltage in the form of pulses to the first working electrode 21 and the first counter electrode 22 that serve as the first electrode pair only at the measurement timing for the first current value during the predetermined period to measure the first current value.

After the three second response values H1, H2, H3 and one first response value G1 are measured, the CPU 72 refers to three conversion matrices to convert them to three blood component amounts. In this case, the three conversion matrices each are prepared beforehand for each of the combinations of the first response value G1 and the second response value H1, the first response value G1 and the second response value H2, as well as the first response value G1 and the second response value H3.

The CPU 72 converts the first response value G1 and the second response value H1 to a blood component amount using the conversion matrix G1-H1 shown in FIG. 17. Similarly, the CPU 72 converts the first response value G1 and the second response value H2 to a blood component amount using the conversion matrix G1-H2 shown in FIG. 18. Similarly, the CPU 72 converts the first response value G1 and the second response value H3 to a blood component amount using the conversion matrix G1-113 shown in FIG. 19.

Specifically, the second or fourth measurement device 6 contains such conversion matrices as those shown in FIGS. 17 to 19 stored in the data storage unit 74. The second or fourth measurement device 6 measures the first response value and the second response values with respect to an unknown blood to obtain a pair of G1 and H1, a pair of G1 and H2, and a pair of G1 and H3. Then, the second or fourth measurement device 6 plots a point determined by the combination of the first response value and a second response value on each conversion matrix and converts said first response value and second response value to a blood component amount. Accordingly, the second or fourth measurement device 6 can obtain the blood component amount with respect to each of the combination of G1 and H1, the combination of G1 and H2, and the combination of G1 and H3.

Next, the second or fourth measurement device 6 compares recorded data including three blood component amounts for the respective pairs of the plurality of first response values and the second response value described above, with the three blood component amounts that are used as measured data. As a result of the comparison, the second or fourth measurement device 6 can extract the recorded data closest to the measured data. The second or fourth measurement device 6 can calculate the blood component amount of the blood from which the recorded data thus extracted was obtained, as the blood component amount of the blood introduced into the biosensor 1.

Figures 20, 21, 22:
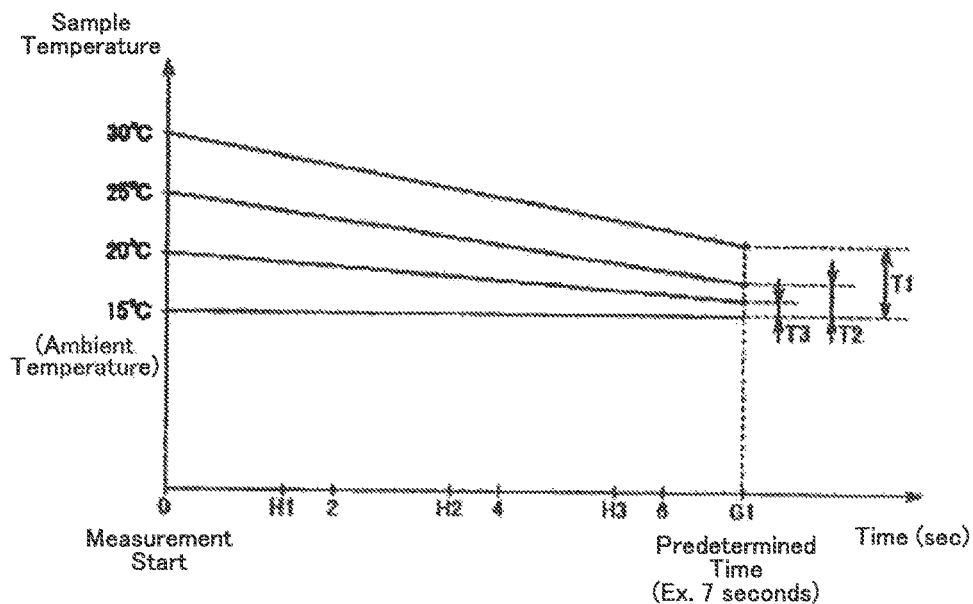
FIG. 20 is a graph showing the temperature change that occurs after the introduction of blood into a biosensor described as another embodiment of the present invention.
FIG. 21 is a table showing the relationships among ambient temperatures, sample introduction temperatures, and blood component amounts that were converted, in a measurement device described as another embodiment of the present invention.
FIG. 22 is a table showing the relationship between a first response value and second response values and the blood component amounts that were converted, per temperature, in a measurement device described as another embodiment of the present invention.

As shown in FIG. 20, the temperature of the blood that is used as a sample introduced into the biosensor 1 decreases according to the elapsed time after the introduction into the biosensor 1. As described above, when the measurement time (the predetermined time) for the blood component amount is set to be seven seconds, how the temperature decreases during the measurement time differs according to the blood temperature measured at the time of the introduction into the biosensor 1. The higher the blood temperature is at the time of the introduction into the biosensor 1, the steeper the slope of the decrease in blood temperature becomes. Furthermore, the blood temperature at the end of the measurement time differs according to the blood temperature measured at the time of the introduction into the biosensor 1. The higher the blood temperature is at the time of the introduction into the biosensor 1, the bigger the difference from the ambient temperature is at the end of the measurement time. For example, when blood with a temperature of 30° C. is introduced into the biosensor 1, the difference in temperature between the blood temperature and the ambient temperature is T1 at the end of the measurement time. Furthermore, when blood with a temperature of 25° C. is introduced into the biosensor 1, the difference in temperature between the blood temperature and the ambient temperature is T2 at the end of the measurement time. When blood with a temperature of 20° C. is introduced into the biosensor 1, the difference in temperature between the blood temperature and the ambient temperature is T3 at the end of the measurement time.

Since the first response value and the second response values measured by the second or fourth measurement device 6 depend on the blood temperature, even when the first response value and the second response value are measured only at the end of the measurement time, accurate first response value and second response value cannot be obtained. Therefore, the second or fourth measurement device 6 measures the first response value multiple times and the second response value only once during the predetermined measurement time. Moreover, the second or fourth measurement device 6 combines the first response values and the second response value arbitrarily and obtains a blood component amount per said arbitrary combination.

The second or fourth measurement device 6 contains recorded data, for example, as shown in FIG. 21 stored in the data storage unit 74. The recorded data includes, as an example, a plurality of blood component amounts obtained from blood, in which the glucose concentration (the first component amount) is 100 mg/dl and the blood cell amount (the second component amount) is 25%, stored per ambient temperature and sample introduction temperature. The sample introduction temperature does not need to be included in the recorded data. Specifically, in the recorded data, an ambient temperature A, a blood component amount Aa1, a blood component amount Aa2, and a blood component amount Aa3 are mapped. The blood component amount Aa1 was converted using the conversion matrix G1-H1 shown in FIG. 17. The blood component amount Aa2 was converted using the conversion matrix G1-H2 shown in FIG. 18. The blood component amount Aa3 was converted using the conversion matrix G1-H3 shown in FIG. 19. It is desirable that the recorded data include the blood component amounts stored for each of a plurality of sample introduction temperatures with respect to the ambient temperature. Furthermore, it is desirable that the recorded data include the blood component amounts stored for each of a plurality of ambient temperatures.

The second or fourth measurement device 6 compares a plurality of blood component amounts, each of which was converted per combination of any one of a plurality of second response values and a first response value, with a plurality of blood component amounts included in the recorded data and thereby can determine the recorded data most approximated. Specifically, when the ambient temperature is near A, the second or fourth measurement device 6 extracts the blood component amounts Aa1 to Aa3, Ab1 to Ab3, and Ac1 to Ac3 of respective combinations corresponding to the ambient temperature A. The second or fourth measurement device 6 compares the blood component amounts of respective combinations that are used as the measured data with the blood component amounts Aa1 to Aa3, Ab1 to Ab3, and Ac1 to Ac3 included in the recorded data that were extracted. The second or fourth measurement device 6 can calculate the glucose concentration of the blood introduced into the biosensor 1 to be 100 mg/dl, when a plurality of blood component amounts included in the measured data are approximated to the blood component amounts Aa1 to Aa3, Ab1 to Ab3, and Ac1 to Ac3 included in the recorded data.

As described above, the second or fourth measurement device 6 can calculate the blood component amount of the blood introduced into the biosensor 1 using a plurality of second response values and one first response value that were measured. Thus, the biosensor system can suppress the errors in measuring the blood component amount.

As described above, the measurement device 6 can calculate the blood component amount of the blood introduced into the biosensor 1 using a plurality of second response values and one first response value that were measured. Thus, the biosensor system can suppress the errors in measuring the blood component amount.

The blood component amounts that are used as the measured data vary depending on the ambient temperature of the biosensor 1. For example, assume that the conversion matrices shown in FIGS. 17 to 19 each were obtained at an environmental temperature of 25° C. As shown in FIG. 22, when blood with a glucose concentration of 125 mg/dl is measured, with the ambient temperature of the biosensor 1 being 25° C., and the second response values H1, I12, I13 and the first response value G1 are converted, the blood component amounts obtained thereby are 125 mg/dl in all combinations. However, when the ambient temperature of the biosensor 1 is 35° C., the blood component amounts are different in all the combinations.

Figures 23, 24, 25:
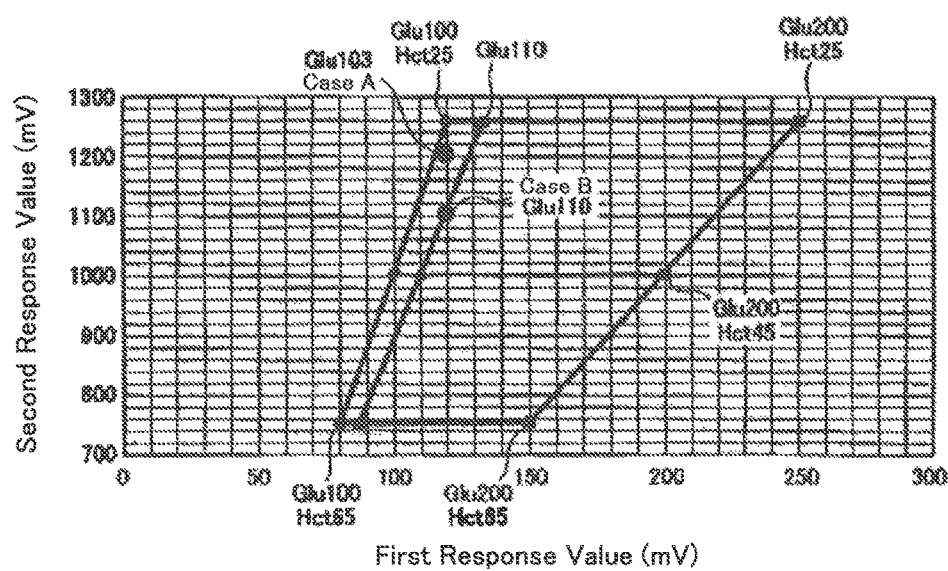
FIG. 23 is a table showing the degree of influence of the glucose concentration on the blood cell amount in a measurement device described as an embodiment of the present invention.
FIG. 24 is a table showing the relationships among known glucose concentrations and blood cell amounts, the degree of influence of temperature, and blood component amounts that were converted, which were obtained when a temperature change occurred in a measurement device described as an embodiment of the present invention.
FIG. 25 is a graph showing the relationship between the first response value and the second response value influenced by temperature, in a measurement device described as an embodiment of the present invention.

Furthermore, when the blood cell amount varies, a glucose concentration is calculated with a variation caused depending on the degree of influence, for example, as shown in FIG. 23. When the glucose concentration is 100 mg/dl, a variation of 25% of the blood cell amount causes the glucose concentration to be calculated with a variation of 20%. Furthermore, when the glucose concentration is 200 mg/dl, the glucose concentration is calculated with a variation of 25%, while the glucose concentration is calculated with a variation of 21% when the glucose concentration is 110 mg/dl.

Moreover, when the temperature around the biosensor 1 changes, the first response value and the second response value that are measured also vary depending on the degree of influence of temperature as shown in FIG. 24, even when blood with a known glucose concentration of 100 mg/dl and a known blood cell amount of 1000 is measured.

As described above, the blood component amount is calculated differently depending on the ambient temperature. Furthermore, in the first measurement device, the third measurement device, the first measurement method, or the third measurement method, the glucose concentration (the first response value) is calculated with a variation depending on the ambient temperature and the blood cell amount (the second component amount). Moreover, in the second measurement device, the fourth measurement device, the second measurement method, or the fourth measurement method, the first response value varies depending on the ambient temperature and the blood cell amount. Therefore, even when bloods with the same glucose concentration are measured and thereby the first response value and the second response value are obtained, the blood component amount varies depending on the case where the measurement is made, as in Cases A, B as shown in FIG. 25. In Case A, the glucose concentration is 103 mg/dl. On the other hand, in Case B, the glucose concentration is 110 mg/dl.

Therefore, it is desirable that the measurement device 6 contain the recorded data stored in the data storage unit 74 per ambient temperature in consideration of the influences of the first response value and the second response value caused by the ambient temperature. The measurement device 6 extracts recorded data close to the current ambient temperature from a plurality of recorded data stored in the data storage unit 74. The measurement device 6 compares a plurality of blood component amounts included in the recorded data extracted according to the current ambient temperature with a plurality of blood component amounts that are used as measured data. Thus, the measurement device 6 can calculate the blood component amount of the blood from which the recorded data most approximated to said measured data was obtained, as the blood component amount of the blood introduced into the biosensor 1.

As described above, in the first measurement device, the third measurement device, the first measurement method, or the third measurement method, the temperature of the blood in the biosensor 1 varies from the time of introduction to the end of measurement, and the first response value varies depending on the second component amount. Therefore, it is desirable that as described above, the first or third measurement device 6 arbitrarily combine a plurality of first response values and a second response value that were measured during a predetermined measurement period to calculate a plurality of blood component amounts. Furthermore, in the second measurement device, the fourth measurement device, the second measurement method, or the fourth measurement method, the temperature of the blood in the biosensor 1 varies from the time of introduction to the end of measurement, and the first response value varies depending on the blood cell amount. Therefore, it is desirable that as described above, the second or fourth measurement device 6 arbitrarily combine one first response value and a plurality of second response values that were measured during a predetermined measurement period to convert them to a plurality of blood component amounts. Thus, even when the blood temperature varies as described above and the second component amount is unknown, the measurement device 6 converts arbitrary combinations of a first response value and a second response value to blood component amounts and then can select recorded data approximated to the blood component amounts that are used as measured data.

Specifically, the first or third measurement device 6 allows the first response value to be measured in a first period included in the first half of the predetermined period and a second period included in the second half of the predetermined period. This makes it possible to obtain a first response value measured when the temperature changes greatly and a first response value measured when the temperature is stable. Furthermore, a second response value measured when the temperature is stable can be obtained. Thus, even if the way of change in the temperature of blood varies each time it is measured, the first or third measurement device 6 can measure a plurality of first response values and a second response value, compare such measured data with recorded data, and calculate the blood component amount. This makes it possible to suppress the effect that the blood component amount varies due to the change in the temperature of blood and thereby an accurate blood component amount cannot be obtained.

Furthermore, specifically, the second or fourth measurement device 6 allows the second response value to be measured in a first period included in the first half of the predetermined period and a second period included in the second half of the predetermined period. This makes it possible to obtain a second response value measured when the temperature changes greatly and a second response value measured when the temperature is stable. Furthermore, a first response value measured when the temperature is stable can be obtained. Thus, even if the way of change in the temperature of blood varies each time it is measured, the second or fourth measurement device 6 can measure a plurality of second response values and a first response value, compare such measured data with recorded data, and calculate the blood component amount. This makes it possible to suppress the effect that the blood component amount varies due to the change in the temperature of blood and thereby an accurate blood component amount cannot be obtained.

It is desirable that in order to improve the accuracy in calculating the blood component amount, the first or third measurement device 6 described above measure more first response values during a predetermined period. The first or third measurement device 6 combines a number of first response values and one second response value, respectively, to obtain a plurality of pairs of a first response value and the second response value. Thus, a number of blood component amounts obtained from a number of the first response values and the second response value that are used as the measured data are compared with a number of the blood component amounts used as the recorded data and thereby the recorded data most approximated to the measured data can be selected. Therefore, the first or third measurement device 6 can obtain recorded data including the blood component amounts closest to a number of measured blood component amounts and then calculate the blood component amount of the blood introduced into the biosensor 1.

Furthermore, it is desirable that in order to improve the accuracy in calculating the blood component amount, the second or fourth measurement device 6 described above measure more second response values during a predetermined period. The second or fourth measurement device 6 combines a number of second response values and one first response value, respectively, to obtain a plurality of pairs of the first response value and a second response value. Thus, a number of blood component amounts obtained from a number of the second response values and the first response value that are used as the measured data are compared with a number of the blood component amounts used as the recorded data and thereby the recorded data most approximated to the measured data can be selected. Therefore, the second or fourth measurement device 6 can obtain recorded data including the blood component amounts closest to a number of measured blood component amounts and then calculate the blood component amount of the blood introduced into the biosensor 1.

As described above, recorded data including a number of blood component amounts is prepared beforehand, and the blood component amount of the blood introduced into the biosensor 1 can be calculated using measured data including a number of the blood component amounts obtained from combinations of the same response values. Therefore, as described above, even when the glucose concentration varies depending on the way of change in the temperature of blood, ambient temperature, or the blood cell amount, the glucose concentration can be calculated with less error by using a number of the blood component amounts.

Next, another embodiment that is different from the embodiment described above is described.

Figure 26:
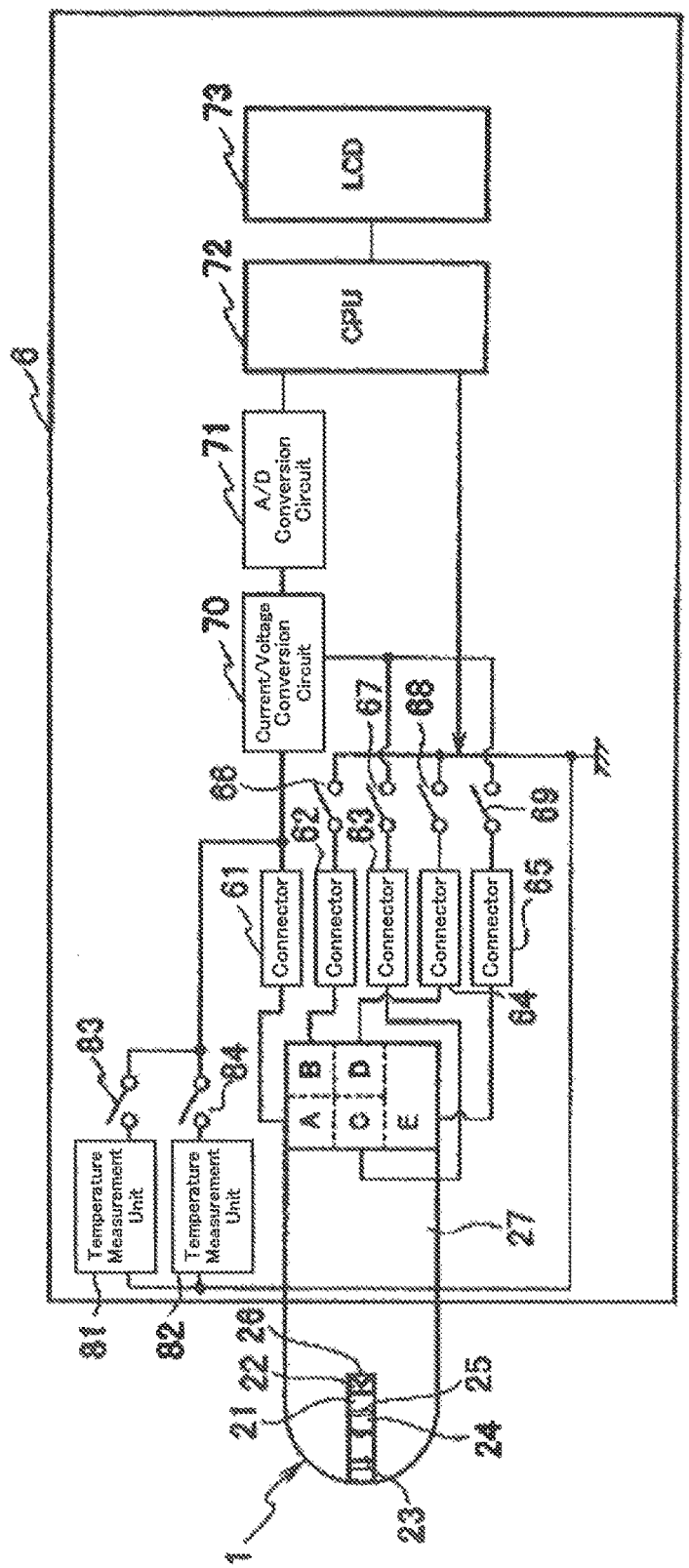
FIG. 26 is a block diagram showing another configuration of a measurement device described as an embodiment of the present invention.

A first or third measurement device 6 described as the present embodiment may calculate the blood component amount of the blood introduced into the biosensor 1 by multivariate analysis carried out using a plurality of blood component amounts obtained by converting at least part of a plurality of first response values and a second response value that were measured. As shown in FIG. 26, the measurement device 6 is different, from the measurement device 6 described above, in not having the data storage unit 74.

Alternatively, a second or fourth measurement device 6 described as the present embodiment may calculate the blood component amount of the blood introduced into the biosensor 1 by multivariate analysis carried out using a plurality of blood component amounts obtained by converting at least part of a plurality of second response values and a first response value that were measured. As shown in FIG. 26, the measurement device 6 is different, from the measurement device 6 described above, in not having the data storage unit 74.

As in the embodiment described above, the first or third measurement device 6 measures a plurality of first response values and a second response value. Alternatively, as in the embodiment described above, the second or fourth measurement device 6 measures a plurality of second response values and a first response value. The CPU 72 converts a part or all of the first response values and the second response value that were measured, to obtain a plurality of blood component amounts. Each blood component amount may denote both the first component amount and the second component amount or one of the first component amount and the second component amount. The CPU 72 carries out multivariate analysis using a plurality of blood component amounts to obtain the blood component amount of the blood introduced into the biosensor 1. The measurement device 6 carries out, for example, multiple regression analysis as the multivariate analysis. The multiple regression analysis uses, as a response function, for example, a multiple regression formula of a linear polynomial such as:

Blood component amount=a1×G1+a2×G2+ . . . +an×Gn+b1×H1+b2×H2+ . . . +bm×Hm+C0.

In the above-mentioned multiple regression formula, G1 to Gn are arbitrary amounts of the first component, H1 to Hm are arbitrary amounts of the second component, a1 to an and b1 to bm are coefficients by which the blood component amount is multiplied, n≠m or n=m holds true, and Co is a constant. By the multiple regression analysis, a process for determining the coefficients in the multiple regression formula is carried out, with a known blood component amount being taken as a target value. That is, the CPU 72 determines the coefficients (a1 to an, b1 to bm), by which a plurality of amounts of the first component and the second component included in the multiple regression formula are multiplied, so as to obtain a highly accurate blood component amount, under conditions in which the ambient temperature and the sample introduction temperature are controlled variously. This gives a response function that is a compensation factor with respect to the temperature influence during measurement, in which the ambient temperature and the sample introduction temperature are incorporated. Accordingly, the CPU 72 determines by regression analysis the compensation formula by which the difference between an intermediate converted value obtained by converting first and second response values and a known blood component amount is made to be zero.

As described above, the measurement device 6 can determine the final blood component amount by calculation carried out using multivariate analysis from a plurality of blood component amounts. Thus, the measurement device 6 can suppress the errors in measuring the blood component amount of the blood introduced into the biosensor 1 as compared to the case where the blood component amount is determined using the first and second response values themselves.

The value determined by multivariate analysis is not limited to blood component amounts. For example, a compensation amount that compensates a converted blood component amount may be determined.

Furthermore, a quadratic polynomial as described below may be used as a response function to be employed as a multiple regression formula.

Glucose Conversion Value = [Formula 1]

$$\beta_0 + \sum_{i=1}^{k} \beta_i x_i + \sum_{i=1}^{k} \beta_{ii} x_i^2 + \sum_{i<j} \beta_{ij} x_i x_j$$

In the measurement device 6 of the present invention, the above-mentioned quadratic polynomial can be formed, with the amounts of the first component (G1 to Gm, where m is the number of the values to be measured) and the amounts of the second component (H1 to Hm, where m is the number of the values to be measured) being arbitrarily combined to be used as each variable xi. As in the case of the above-mentioned linear polynomial, the coefficients of the quadratic polynomial are determined by learning processing.

In this connection, in the above-mentioned quadratic polynomial, when 18 pairs of the amounts of the first component and the amounts of the second components are selected in total to generate the conversion formula or the compensation formula for the blood component amount, the number of the terms of the compensation formula is 190 terms (including constant terms).

When each coefficient is actually to be determined, higher-order terms (for example, xi2 and xixj) can be subjected to variable conversion to be dealt as a first-order term of a parameter. Actual calculation used in determining the coefficients is the same as that used in the case of the above-mentioned linear polynomial. Furthermore, the variables of the quadratic polynomial may also include ambient temperature measured by the measurement device 6 described above in addition to the above-mentioned amounts of the first component and the second component.

When the conversion formula or the compensation formula for the blood component amount is formed as a quadratic polynomial, a compensation formula with less actual error and distribution of each term can often be obtained as compared to the case of the linear polynomial.

Furthermore, the above-mentioned quadratic polynomial is equivalent to an approximation function obtained when the hypersurface indicating distribution in a multidimensional space in which each variable is used as an axis is Taylor-expanded up to the quadratic term, of the blood component amount that is introduced into the above-mentioned compensation formula. That is, as long as the fact that the estimated distribution is continuous is secured in principle, it is possible to obtain sufficient accuracy in principle when the above-mentioned quadratic polynomial is applied to a sufficiently narrow region of respective variables (selected groups of the first component amounts and the second component amounts). Variables of higher order can also be used, but when response values of the same amount are combined, the number of the terms of the conversion formula or the compensation formula for the blood component amount further increases. This causes disadvantages that the calculation process becomes complicated or the number of minimum data required for determining the coefficients increases.

Furthermore, an example in which a linear regression formula is used was described as the form of the conversion formula or the compensation formula for the blood component amount described above. However, the regression formula does not always need to be linear. It may be formed by linear addition of terms of variables xi, which were determined using the blood component amount and ambient temperature, combined through arbitrary operators. In this case, when the regression analysis is carried out for determining the coefficient of each term, each term is subjected to variable conversion to be a linear formula of parameters as in the case of the linear polynomial and quadratic polynomial. Accordingly, it can be carried out by applying the method of the multiple regression analysis of a linear polynomial.

The above-mentioned embodiments are examples of the present invention. Therefore, the present invention is not limited to the above-mentioned embodiments and it should be appreciated that even in the case other than the embodiments, various changes can be made depending on the design, etc., as long as they are in the range that does not depart from the technical ideas of the present invention.

That is, in the above-mentioned embodiments, a plurality of blood component amounts that were used as measured data were compared with a plurality of blood component amounts that were used as recorded data and thereby the recorded data most approximated was obtained. However, a plurality of glucose concentrations that are used as measured data may be compared with a plurality of glucose concentrations that are used as recorded data. Furthermore, a plurality of blood cell amounts that are used as measured data may be compared with a plurality of blood cell amounts that are used as recorded data.

DESCRIPTION OF THE NUMERALS

1 Biosensor
2 Blood Component Measurement Layer
6 Measurement Device
21 First Working Electrode (First Electrode Pair)
22 First Counter Electrode (First Electrode Pair)
23 Second Working Electrode (Second Electrode Pair)
24 Second Counter Electrode (Second Electrode Pair)
25 Non-Interference Portion
26 Detection Electrode
72 CPU (Measurement Means, Control Means, Calculation Means)
74 Data Storage Unit (Storage Means)
81, 82 Temperature Measurement Units

The invention claimed is:
1. A blood component measurement device that measures a blood component amount using a biosensor into which blood is introduced wherein the blood component contained in said blood is subjected to oxidation-reduction reaction using an oxidoreductase, wherein the blood component measurement device includes:
  (a) a first current value measuring device that detects, as a first current value, an oxidation-reduction current that is generated by the oxidation-reduction reaction when a first voltage is applied to a first electrode pair in the biosensor;
  (b) a second current value measuring device that detects, as a second current value, a current that is generated when a second voltage is applied to a second electrode pair in the biosensor;
  (c) a controller that exerts control so that within a predetermined period after the introduction of the blood into the biosensor, the controller applies the second voltage to the second electrode pair in the form of pulses, so that the second current value is measured multiple times and the first current value is measured after the application of the second voltage;
  (d) a converter that converts, to blood component amounts, pairs of the first current value measured by the first current value measuring device and any one of a plurality of second current values measured by the second current value measuring device; and
  (e) a calculator that calculates the blood component amount for the blood introduced into the biosensor, using a plurality of the blood component amounts converted by the converter.

2. The blood component measurement device according to claim 1, wherein the blood component measurement device includes a memory that contains recorded data, stored per blood in which the blood component amount is known, including a plurality of the blood component amounts converted from the pairs of current values, and
  wherein the calculator compares the recorded data with measured data including a plurality of the blood component amounts converted by the converter and calculates the blood component amount from recorded data closest to said measured data, as the blood component amount of the blood introduced into the biosensor.

3. The blood component measurement device according to claim 2, wherein the calculator compares a plurality of blood component amounts converted from arbitrary combinations of the first current value and the second current value selected from the pairs of current values measured as a result of the control exerted by the controller, with recorded data of a plurality of blood component amounts converted from the same combinations as the arbitrary combinations of the first current value and the second current value stored in the memory, and calculates the blood component amount from the closest recorded data, as the blood component amount of the blood introduced into the biosensor.

4. The blood component measurement device according to claim 1, wherein the blood component measurement device further includes:
  (a) a memory that contains recorded data, stored per blood sample in which the blood component amount is known and per ambient temperature, including a plurality of the blood component amounts converted from the pairs of current values, and
  (b) a temperature detector that detects the ambient temperature,
  wherein the calculator (i) extracts a plurality of recorded data obtained at a temperature near the ambient temperature detected by the temperature detector, (ii) compares said plurality of recorded data thus extracted with measured data including the plurality of the blood component amounts converted by the converter, and (iii) calculates the blood component amount from the recorded data closest to said measured data, as the blood component amount of the blood introduced into the biosensor.

* * * * *